US009556149B2

(12) United States Patent
Krishnan et al.

(10) Patent No.: US 9,556,149 B2
(45) Date of Patent: Jan. 31, 2017

(54) PROCESSES FOR THE PREPARATION OF PYRAZOLE DERIVATIVES USEFUL AS MODULATORS OF THE 5-HT2A SEROTONIN RECEPTOR

(71) Applicant: Arena Pharmaceuticals, Inc., San Diego, CA (US)

(72) Inventors: Ashwin M. Krishnan, San Diego, CA (US); Tawfik Gharbaoui, Escondido, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 14/523,224

(22) Filed: Oct. 24, 2014

(65) Prior Publication Data

US 2015/0045372 A1    Feb. 12, 2015

Related U.S. Application Data

(63) Continuation of application No. 12/936,038, filed as application No. PCT/US2009/002019 on Apr. 1, 2009, now abandoned.

(60) Provisional application No. 61/072,697, filed on Apr. 2, 2008.

(51) Int. Cl.
*C07D 403/06* (2006.01)
*C07D 241/04* (2006.01)

(52) U.S. Cl.
CPC ........... *C07D 403/06* (2013.01); *C07D 241/04* (2013.01)

(58) Field of Classification Search
CPC ...................... C07D 403/06; C07D 241/04
See application file for complete search history.

(56) References Cited

U.S. PATENT DOCUMENTS

| | | | |
|---|---|---|---|
| 4,099,012 A | 7/1978 | Gschwend |
| 4,405,644 A | 9/1983 | Kabbe et al. |
| 4,409,231 A | 10/1983 | Stenzel et al. |
| 4,985,352 A | 1/1991 | Julius et al. |
| 5,077,409 A | 12/1991 | Wissner |
| 5,128,351 A | 7/1992 | Wissner |
| 5,523,280 A | 6/1996 | Chene et al. |
| 5,661,024 A | 8/1997 | Kao et al. |
| 5,885,785 A | 3/1999 | Kao et al. |
| 5,886,044 A | 3/1999 | Widdowson et al. |
| 5,905,080 A | 5/1999 | Duckworth et al. |
| 5,945,382 A | 8/1999 | Cantegril et al. |
| 5,990,133 A | 11/1999 | Gaster et al. |
| 6,005,008 A | 12/1999 | Widdowson |
| 6,028,085 A | 2/2000 | Bromidge |
| 6,054,472 A | 4/2000 | Armistead et al. |
| 6,107,324 A | 8/2000 | Behan et al. |
| 6,140,509 A | 10/2000 | Behan et al. |
| 6,150,393 A | 11/2000 | Behan et al. |
| 6,271,261 B1 | 8/2001 | Widdowson |
| 6,297,261 B1 | 10/2001 | Christophersen et al. |
| 6,358,698 B1 | 3/2002 | Weiner et al. |
| 6,383,762 B1 | 5/2002 | Kao et al. |
| 6,417,393 B1 | 7/2002 | Christophersen et al. |
| 6,420,541 B1 | 7/2002 | Behan et al. |
| 6,479,480 B1 | 11/2002 | Moyes et al. |
| 6,479,519 B1 | 11/2002 | Astles et al. |
| 6,531,291 B1 | 3/2003 | Kabbash et al. |
| 6,541,209 B1 | 4/2003 | Behan et al. |
| 6,696,475 B2 | 2/2004 | Dahl et al. |
| 6,706,749 B2 | 3/2004 | Dahl et al. |
| 6,784,183 B2 | 8/2004 | Lavielle et al. |
| 6,846,919 B2 | 1/2005 | Behan et al. |

(Continued)

FOREIGN PATENT DOCUMENTS

| | | |
|---|---|---|
| CA | 2135253 | 5/1996 |
| EP | 1 108 720 | 6/2001 |

(Continued)

OTHER PUBLICATIONS

"Arena Pharmaceuticals Announces Preliminary Results of Phase 2b Clinical Trial of APD125 for the Treatment of Insomnia" PRNewswire-First Call via COMTEX News Network, Press Release dated (Dec. 9, 2008).
Adams et al; "Antithrombotic and Vascular effects of AR246686, a novel 5-HT2A receptor antagonist" EJM, pp. 1-22 (2007).
Affolter, H., "CA2+ as Messenger of 5HT2-Receptor Stimulation in Human Blood Platelets," Naunyn Schmiedebergs Arch. Pharmacol., 1984, vol. 325(4), 337-42.
Al-Shamma et al., "Nelotanserin, a Novel Selective Human 5-Hydroxytryptamine 2A Inverse Agonist for the Treatment of Insomnia," *J Pharmacol. Exp. Ther*., 2010, 332:281-290.
Al-Shamma et al; "The Selective Serotonin 5HT2A Inverse Agonist APD125 Promotes Sleep Onset and Consolidation in Male Wistar Rats During the Normal Active Phase" APSS abstract (2004).

(Continued)

*Primary Examiner* — Alexander R Pagano
*Assistant Examiner* — Ebenezer O Sackey
(74) *Attorney, Agent, or Firm* — Pepper Hamilton LLP

(57) ABSTRACT

The present invention relates to processes for preparing pyrazole derivatives of Formula (I) and salts and pharmaceutical compositions of the salts thereof, useful as modulators of 5-HT$_{2A}$ serotonin receptor activity.

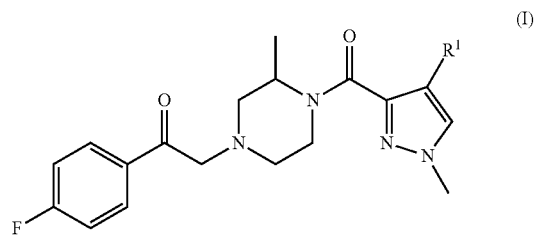

(I)

The present invention also relates to intermediates used in the processes, and their preparation. The present invention also relates to salts of compounds of Formula (I) and pharmaceutical compositions thereof.

21 Claims, No Drawings

(56) References Cited

U.S. PATENT DOCUMENTS

| | | | |
|---|---|---|---|
| 7,368,539 B2 | 5/2008 | Behan et al. | |
| 8,481,535 B2* | 7/2013 | Gharbaoui | C07D 231/12 514/236.5 |
| 2002/0025965 A1 | 2/2002 | Lavielle et al. | |
| 2002/0098548 A1 | 7/2002 | Kao et al. | |
| 2004/0102636 A1 | 5/2004 | Miller et al. | |
| 2005/0054691 A1 | 3/2005 | Potter et al. | |
| 2005/0080124 A1 | 4/2005 | Teegarden et al. | |
| 2005/0267097 A1 | 12/2005 | Pinto et al. | |
| 2006/0014705 A1 | 1/2006 | Howitz et al. | |
| 2006/0063754 A1 | 3/2006 | Edgar et al. | |
| 2006/0205792 A1 | 9/2006 | Wong et al. | |
| 2006/0229335 A1 | 10/2006 | Teegarden et al. | |
| 2007/0004750 A1 | 1/2007 | Lorsbach et al. | |
| 2007/0037827 A1 | 2/2007 | Nunes et al. | |
| 2007/0072857 A1 | 3/2007 | Teegarden et al. | |
| 2007/0207994 A1 | 9/2007 | Teegarden et al. | |
| 2007/0244086 A1 | 10/2007 | Teegarden et al. | |
| 2008/0015223 A1 | 1/2008 | Strah-Pleynet et al. | |
| 2008/0200530 A1 | 8/2008 | Unett et al. | |
| 2009/0053306 A1 | 2/2009 | Agarwal et al. | |
| 2009/0076254 A1 | 3/2009 | Behan et al. | |
| 2009/0186895 A1 | 7/2009 | Teegarden et al. | |
| 2009/0197935 A1 | 8/2009 | Teegarden et al. | |
| 2010/0004264 A1 | 1/2010 | Xiong et al. | |
| 2010/0240653 A1 | 9/2010 | Santora et al. | |

FOREIGN PATENT DOCUMENTS

| | | |
|---|---|---|
| EP | 1 558 582 | 8/2005 |
| EP | 1 734 039 | 12/2006 |
| WO | WO 96/02138 | 2/1996 |
| WO | WO 96/10559 | 4/1996 |
| WO | WO 96/23783 | 8/1996 |
| WO | WO 97/03967 | 2/1997 |
| WO | WO 97/45111 | 12/1997 |
| WO | WO 98/24785 | 6/1998 |
| WO | WO 99/06354 | 2/1999 |
| WO | WO 99/32436 | 7/1999 |
| WO | WO 99/32463 | 7/1999 |
| WO | WO 99/52927 | 10/1999 |
| WO | WO 00/57877 | 10/2000 |
| WO | WO 00/64866 | 11/2000 |
| WO | WO 01/21160 | 3/2001 |
| WO | WO 01/29008 | 4/2001 |
| WO | WO 02/39987 | 5/2002 |
| WO | WO 02/051833 | 7/2002 |
| WO | WO 02/076464 | 10/2002 |
| WO | WO 03/062206 | 7/2003 |
| WO | WO 2004/028450 | 4/2004 |
| WO | WO 2004/045118 | 5/2004 |
| WO | WO 2004/058722 | 7/2004 |
| WO | WO 2004/071426 | 8/2004 |
| WO | WO 2004/085433 | 10/2004 |
| WO | WO 2004/096771 | 11/2004 |
| WO | WO 2005/012254 | 2/2005 |
| WO | WO 2005/077345 | 8/2005 |
| WO | WO 2005/103011 | 11/2005 |
| WO | WO 2006/018662 | 2/2006 |
| WO | WO 2006/049734 | 5/2006 |
| WO | WO 2006/049941 | 5/2006 |
| WO | WO 2006/055734 | 5/2006 |
| WO | WO 2006/059149 | 6/2006 |
| WO | WO 2006/060654 | 6/2006 |
| WO | WO 2006/070394 | 7/2006 |
| WO | WO 2006/076592 | 7/2006 |
| WO | WO 2006/078610 | 7/2006 |
| WO | WO 2006/079637 | 8/2006 |
| WO | WO 2006/081335 | 8/2006 |
| WO | WO 2006/086705 | 8/2006 |
| WO | WO 2006/089871 | 8/2006 |
| WO | WO 2006/095205 | 9/2006 |
| WO | WO 2006/097766 | 9/2006 |
| WO | WO 2006/100519 | 9/2006 |
| WO | WO 2006/112464 | 10/2006 |
| WO | WO 2006/116614 | 11/2006 |
| WO | WO 2007/002559 | 1/2007 |
| WO | WO 2007/026959 | 3/2007 |
| WO | WO 2007/120600 | 10/2007 |
| WO | WO 2007/129111 | 11/2007 |
| WO | WO 2007/136680 | 11/2007 |
| WO | WO 2007/136703 | 11/2007 |
| WO | WO 2007/136875 | 11/2007 |
| WO | WO 2008/027483 | 3/2008 |
| WO | WO 2008/042388 | 4/2008 |
| WO | WO 2008/054748 | 5/2008 |
| WO | WO 2009/023253 | 2/2009 |
| WO | WO 2010/062321 | 6/2010 |

OTHER PUBLICATIONS

Al-Shamma; "APD125: A 5-HT2A Inverse Agonist for the Treatment of Sleep Maintenance Insomnia" DDST; pp. 1-7 (2008).

Al-Shamma; "The Selective Serotonin 5HT2A Inverse Agonist APD125 Promotes Sleep Onset and Consolidation" APSS, pp. 1-5, (Jun. 22, 2005).

Andrzejewska-Buczko et al., "[Serotonin in Diabetic Retinopathy]," Klin Oczna. Feb. 1996: 98(2): 101-4 (abstract only provided).

Antinori et al., Neurology, 48: 687-694 (1997).

Barluenga, Jr. et al., "A New and Specific Method for the Monomethylation of Primary Amines," *J Chem. Soc. Chem. Commun.*, 1984, 20, 1334-1335.

Batey, R.A. et al., "An Efficient New Protocol for the Formation of Unsymmetrical Tri-and Tetrasubstituted Ureas," *Tetra. Lett.*, 1998, 39, 6267-6270.

Berge et al., "Pharmaceutical Salts," *J of Pharmaceutical Sciences* (1977) 66(1):1-19.

Berger, et al., Seminars in Neurology, 19: 193-200 (1999).

Bernatowicz, M. et al., "A Comparison of Acid Labile Linkage Agents for the Synthesis of Peptide C-Terminal Amides," *Tetra. Lett.*, 1989, 30(35), 4645-4648.

Blier, P. et al., "Putative Mechanisms of Action of Antidepressant Drugs in Affective and Anxiety Disorders and Pain," *Journal of Psychiatry and Neuroscience*, 2000, vol. 26(1), 37-43.

Cameron et al., "The Effects of 5-Hydroxytryptamine 5-H'IR Receptor Antagonists on Nerve Conduction Velocity and Endoneurial Perfusion in Diabetic Rats.," Naunyn Schmiedebergs Arch Pharmacol., Jun. 2003; 367(6):607-14.

Carter, H.E. et al., "Carbobenzoxy Chloride and Derivatives, " *Org. Syn. Coll.*, 1955, vol. 3, 167-169.

Casey et al. "Constitutively Active Mutant $5HT_2a$ Serotonin Receptors: Inverse Agonist Activity of Classical $5-HT_{2a}$ Antagonists," Society for Neuroscience Abstracts, vol. 22, p. 699.10 (1996).

Catalan, J. et al., "New Ultraviolet Stabilizers: 3- and 5-(2'-Hydroxyphenyl)pyrazoles," *J Am. Chem. Soc.*, 114, 5039-5048 (1992).

Cazzola, M. et al., "5-HT Modifiers as a Potential Treatment of Asthma," TiPS, 21:13-6 (2000).

Cazzola, M. et al., Trends Pharmacol. Sci. 21: 201-202 (2000).

Chang et al., "Mechanism of the Ocular Hypotensive Action of Ketanserin,"] Ocul Pharmacol., 1985 Summer; 1(2):137-47.

Chang, C. et al., Shock, 24(4): 336-340 (2005).

Cohen-Mansfield et al., "Agitated Behaviors in the Elderly. I.A. Conceptual Review," J Am Geriatr Soc., Oct. 1986;34(10):711-21.

Collier et al., "Radiosynthesis and In-Vivo Evaluation of the Psuedopeptide 6-0pioid Antagonist [$^{125}$I]-ItIPP(ψ)"*J Labeled Compd. Radiopharm.*, 1999, vol. 42, pp. S264-S266.

De Bie et al., "Modulation of Airway Hyperresponsiveness and Eosinophilia by Selective Histamine and 5-HT Receptor Antagonists in a Mouse Model of Allergic Asthma," British Journal of Pharmacology, 1998, vol. 124, 857-864.

Deuchar, G., et al., Pulm. Pharmacol. Ther., 18(1): 23-31 (2005).

Dosa et al; "Solubilized phenyl-pyrazole ureas as potent, selective 5-HT2A inverse-agonists and their application as antiplatelet agents" BMCL; pp. 1-15 (2010).

(56) References Cited

OTHER PUBLICATIONS

Dosa et al; "Synthesis and SAR of Pyridinyl-Pyrazole Derivatives as Selective 5HT2A Inverse- Agonists for Platelet Aggregation", 235th ACS National Meeting, MEDI 44 (poster) (2008).
Dosa et al; "Synthesis and SAR of Solubilized Pyrazole Derivatives as 5HT2A Inverse-Agonists for Platelet Aggregation" ACS; 232nd ACS National Meeting, MEDI 431 (poster) (2006).
Elliott, J. M. et al., "4-Oxospiro[benzopyran-2,4'-piperidines] as Class III Antiarrhythmic Agents. Pharmacological Studies on 3,4-Dihydro-1'-[2-(benzofurazan-5-y1)-ethyl]-6methanesulfonamidospiro[(2H)-1-benzopyran-2,4'-piperidin]-4-one (L-691, 121)", *J Med. Chem.*, 35:3973-3976 (1992).
Elphick, G. et al., "The Human Polyomavirus, JCV, Uses Serotonin to Infect Cells," *Science*, 2004, vol. 306, 1380-3.
Fujita, M. et al., Am. Heart J. 145: el6 (2003).
Fujiwara, T. et al., Journal of Cardiovascular Pharmacology 26: 503-510 (1995).
Grunder et al., Time Course of 5-HT2A Receptor Occupancy in the Human Brain After a Single Oral Dose of the Putative Antipsychotic Drug MDL 100,907 Measured by Position Emission Tomography, Neuropsychopharmacology. Sep. 1997; 17(3):175-85.
Guillory, K.J., Generation of Polymorphs, Hydrates, Solvates, and Amorphous Solids; Polymorphism in Pharmaceutical Solids, ed. Harry G. Brittan, vol. 95, 202-209 (1999).
Gutsche, C.D. et al., "2-Phenylcycloheptanone," *Org. Syn. Coll.*, 1963, vol. 4, 780-783.
Hayashi, T. et al., Atherosclerosis 168: 23-31 (2003).
Herrick-Davis et al., "Activating Mutations of the Serotonin 5-HT2 Receptor," J Neurochem, Sep. 1997; 69(3):1138-44.
Herrick-Davis et al., "Constitutively active 5HT2C Serotonin receptor Created by Site-Directed Mutagenesis," Society for Neuroscience Abstracts, vol. 22, p. 699.18 (1993).
Hittner et al; "A Selective 5-HT2A Receptor Inverse Agonist with Preclinical Antipsychotic Profile in Rats" 2000 NEURO poster (2000).
Holtje, The Practice of Medicinal Chemistry, 2nd ed., 2003, Wermuth (editor), Academic Press, pp. 387-403.
Horibe, E., Circulation Research 68: 68-72 (2004).
Ieni, J. and Meyerson, L., "The 5-HT1A Receptor Probe[3H]8-OH-DPAT Labels . . . ," *Life Sciences*, 1988, vol. 42, 311-320.
Ikeguchi, K. and Kuroda, A., "Mianserin Treatment of Patients with Psychosis Induced by Antiparkinsonian Drugs," *Eur. Arch. Psych. Clin. Neurosci.*, 1995, 244, 320-324.
Jayakumar et al; "Synthesis and SAR of Alkoxyphenyl Pyrazole as 5-HT2A Inverse Agonists" 2006, ACS, 232nd ACS National Meeting, MEDI 430.
Jayakumar et al; "Synthesis and SAR of Novel-Phenyl-Pyrazole Urea derivatives" 2006 ACS.
Jayakumar et al; "Synthesis and SAR of Substituted Diphenylamines as 5HT2A Inverse-Agonists" 2004 ACS.
Jayakumar et al; "Synthesis and SAR of Substituted Diphenylamines as 5HT2A Inverse-Agonists" 2005 ACS, 229th ACS National Meeting, MEDI 049.
Julius, D. et al., "The 5HT2 Receptor Defines a Family of Structurally Distinct but Functionally Conserved Serotonin Receptors," Proc. Natl. Acad. Sci. USA, 1990, vol. 87, 928-932.
Kanayama, M. et al,. "New Treatment of Lumbar Disc Herniation Using 5-hydroxytryptamine2a Receptor Inhibitor: a Randomized Controlled Trial," Journal of Neurosurgery: Spine, 2005, vol. 2, 441-6.
Katz et al., "Comparison of Risperidone and Placebo for Psychosis and Behavioral Disturbances Associated with Dementia: a Randomized, Double-Blind Trial. Risperidone Study Group," J Clin Psychiatry. Feb. 1999;60(2):107-15.
Kitagawa, 0. et al., "Beckmann Rearrangement of O-4 Pentenyl Oxime through*N*-Bromosuccinimide-Mediated Activating Process", *Chem. Pharm. Bull.*, 45(1) 32-35 (1997).
Konig, W. et al., "A New Method for Synthesis of Peptides: Activation of the Carboxyl Group with Dicyclohexylcarbodiimide Using 1-Hydroxybenzotriazoles as Additives," *Chem. Ber.*, 1970, 103, 788-798 (English abstract included).
Koss et al., "Assessing Patterns of Agitation in Alzheimer's Disease Patients with Cohen-Mansfield Agitation Inventory. The Alzheimer's Disease Cooperative Study," Alzheimer Dis Assoc Disord. 1997;11 Suppl. 2: S45-50.
Krieger, et al., Pediatr. Transplantation; 8: 594-599 (2004).
Krystal et al; "The Effects of APD125, a Selective Serotonin 5-HT2A, on Sleep Quality and Sleep Maintenance in a Subjective Study in Patients with Primary Insomnia" SLEEP; pp. 1-23 (2009).
Landolt et al., "Serotonin-2 Receptors and Human Sleep: Effective of a Selective Antagonist on EEG Power Spectra," Neuropsychopharmacology, Sep. 1999; 21(3):455-66.
Le Bas et al., "Radioiodinated Analogs of EP 00652218 for the Exploration of the Tachykinin NKI Receptor by Spect," *J Labeled Compd. Radiopharm.*, 2001, vol. 44, pp. S280-S282.
Luthringer et al; "Pharmacokinetic and Pharmacodynamic Effects of the Selective 5HT2A Inverse Agonist APD125 in Healthy Adults" 2005 APSS.
Major, et al. Proc. Natl. Acad. Sci. USA, 82: 1257-1261 (1985).
Mandel, John, "Statistical Analysis of Experimental Data", Chapter 3, pp. 28-57, Toronto, Ontario, (1964).
Mandel, John, "Statistical Analysis of Experimental Data", Chapter 9, pp. 204-207, Toronto, Ontario, (1964).
Marchini, P. et al., "Sodium Borohydride-Carboxylic Acid Systems. Useful Reagents for the Alkylation of Amines," *J Org. Chem.*, 1975, 40(23), 3453-3456.
Marcos, E., et al., Circ. Res. 94(9): 1263-70 (2004).
Mastropasqua et al., "Ocular Hypotensive Effect of Ketanserin in Patients with Primary Open Angle Glaucoma," Acta Ophthalmol Scand Suppl., 1997(224):24-5.
Menzaghi et al; "AR116081, A Novel Selective 5-HT2A Inverse Agonist As a Putative Atypical Antipsychotic: Comparative Studies with Clozapine and Haloperidol" CINP poster (2000).
Menzaghi et al; "AR116081, A Novel High Affinity 5-HT2A Receptor Inverse Agonist With In Vivo Efficacy" Nov. 1999 NEURO.
Menzaghi et al; "Identification of Novel Selective 5-HT2A Inverse Agonists As Putative Atypical Antipychotics Using Constitutively Activated Human 5-HT Receptors" ASPET poster (Jun. 2000).
Menzaghi et al; "Therapeutic Potential of Selective Serotonin 5HT2A Receptor Inverse Agonists: Pre-Clinical Evaluation of AR116081 As Antipsychotics in Rodents" 2002 FESN abstract (2002).
Miao, C., Clin. Exp. Pharmacol. Physiol, 30(3): 189-193 (2006).
Mizuki, Y. et al., "Effects of Mianserin on Negative Symptoms in Schizophrenia," *Int. Clinical Psychopharmacology*, 1990, 5: 83-95.
Morissette et al., Advanced Drug Delivery Reviews 56 (2004) 275-300.
Mueller, Ann. Thorac. Surg. 77: 354-362 (2004).
Muto, T. et al., "Protective Effects of Sarpogrelate, a 5HT2A Antagonist, Against Postischemic Myocardial Dysfunction in Guinea-Pig Hearts," *Molecular and Cellular Biochemistry*, 2005, vol. 272, 119-32.
National Institutes of Health, "*Facts about Insomnia*,"NIH Publication No. 95, 1995, 3801, p. 1-4.
Newton, R.A. and Elliot, J.M., "Mianserin-Induced Down-Regulation of Human 5-Hydroxytryptamine2A and 5-Hydro . . . ,"*Journal of Neurochemistry*, 1997, 69: 1031-1038.
Nishiyama, T., "Effects of 5HT2A Receptor Antagonist, Sarpogrelate on Thermal or Inflammatory Pain," *European Journal of Pharmacology*, 2005, vol. 516, 18-22.
Nomura, S. et al., "5HT2A Receptor Antagonist Increases Circulating Adiponectin in Patients with Type 2 Diabetes," *Blood Coagulation and Fibrinolysis*, 2005, vol. 16(6), 423-8.
Pawlak, D. et al., Thrombosis Research 90: 259-270 (1998).
Pietraszek et al., "Blood Serotonergic Mechanisms in Type 2 (Non-Insulin-Dependent) Diabetes Mellitus," Thromb Res., Jun. 15, 1992;66(6):765-74.
Portegies, et al., Eur. *J Neural.*, 11: 297-304 (2004).

(56) References Cited

OTHER PUBLICATIONS

Prosser et al., "Selective Serotonin 5-HT2A Inverse Agonists Promote Sleep Consolidation in Male Wistar Rats During the Normal Inactive Phase," #29, Arena Pharmaceuticals, Inc., Meeting (Jun. 2004) 1 page.
Querbes, et al., *J Virology*, 78: 250-256 (2004).
Rosenberg et al; "APD125, A Selective Serotonin 5-HT2A Receptor Inverse Agonist, Significantly Improves the Key Parameters of Sleep Maintenance in Patients with Primary Insomnia" AASM abstract (2007).
Rosenberg et al; "APD125, A Selective Serotonin 5-HT2A Receptor Inverse Agonist, Significantly Improves the Key PSG Parameters of Sleep Maintenance in Patients with Primary Insomnia", APA poster (2008).
Rosenberg et al; APD125, A Selective Serotonin 5-HT2A Receptor Inverse Agonist, Significantly Improves Sleep Maintenance in Primary Insomnia SLEEP, DD. 1-37 (2008).
Roth et al; "APD125, A Selective Serotonin 5-HT2A Receptor Inverse Agonist, Significantly Improves the Key Parameters of Sleep Maintenance in Patients with Primary Insomnia" APSS pp. 1-19 (2008).
Sahgal, A. (ed.), "Practical Behavioural Neuroscience: Problems, Pitfalls and Suggestions," in *Behavioral Neuroscience: A Practical Approach*, IRL Press, New York, 1993, vol. 1, 1-8.
Satomura et al., "Sarpogrelate, a Specific 5 HT2-Receptor antagonist, Improves the Coronary Microcirculation in Coronary Artery Disease," Clin Cardiol. Jan. 2002; 25(1):28-32.
Sawnyok, J. et al., "Antidepressants as Analgesics: an Overview of Central and Peripheral Mechanisms of Action," *Journal of Psychiatry and Neurosciences*, 2001, vol. 26(1), 21-9.
Schmidt, C., "The Role of 5-HT2A Receptors in Antipsychotic Activity," *Life Sciences*, 1995, 56(25), 2209-2222.
Shan et al; "Investigation of Non-Aqueous Vehicles for a Poorly Soluble Compound Intended for Softgel Dosage Form Development" 2005.
Shan et al; "Physicochemical Characterization During Salt Selection Process" 2005 AAPS.
Shan et al; "Physicochemical Characterization During Salt Selection Process" 2006 AAPS.
Sharpley et al., Slow Wave Sleep in Humans: Role of 5-HT2A and 5-HT2C Receptors. Neuropharmacology. Mar.-Apr. 1994;33(3-4):467-71.
Sheehan, J.C. et al., "1-Ethyl-3-(3-Dimethylamino) Propylcarbodiimide Hydrochloride and Methiodide," *Org. Syn. Coll.*, 1973, vol. 5, 555-558.
Shibata, R. et al., "Adiponectin Protects Against Myocardial Ischemiareperfusion Injury Through AMPK- and COX-2 Dependent Mechanisms," *Nature Medicine*, Advanced Online Publications: pp. 1-8, Published Online Sep. 11, 2005.
Silva, A. Eur, *J Pharmacol.*, 518(2-3): 152-7 (2005).
Singh, et al., Transplantation, 69: 467-472 (2000).
Smith et al., Test-Retest Variability of Serotonin 5-HT2A Receptor Binding Measured with Positron Emission Tomography and [18F]altanserin in the Human Brain, Synapse, Dec. 1998;30(4):380-92.
Sorenson et al., "Characterization of the 5-HT2 Receptor Antagonist MDL 100907 as Putative Atypical Antipsychotic: Behavioral, Electrophysiological and Neurochemical Studies," *J Pharacol.* Exp. Ther., 1993 266(2), 684-691.
Speer et al; "Influence of Digestive Enzymes Combined with Sodium Lauryl Sulfate on Dissolution of Cross-linked Gelatin Capsules" 2005 AAPS.
Speer et al; "Influence of Digestive Enzymes on Dissolution of a Poorly Water Soluble Compound From Cross-Linked Gelatin Capsules in Sodium Lauryl Sulfate Medium" 2005 AAPS.
Speer et al; Intrinsic Dissolution Characterization of Different Morphic Forms of a Poorly Water Soluble Compound 2006 AAPS.

Staley et al., Comparison of [(18)F]altanserin and [(18)F]deuteroaltanserin for PET Imaging of Serotonin(2A) Receptors in Baboon Brain: Pharmacological Studies., Nucl Med Biol., Apr. 2001; 28(3):271-9.
Strah-Pleynet et al., "Discovery and SAR of Novel 5-HT$_{2A}$ Inverse-Agonists," 227 ACS National Meeting, MEDI 270, Arena Pharmaceuticals Inc. (Mar. 2004), 1 page.
Strah-Pleynet et al; "Biososteric Modifications of Urea Derivatives as 5HT2A Inverse-Agonists" 2004 ACS.
Strah-Pleynet t et al; 5HT2A Receptor Inverse Agonists: Design and SAR of Novel Pyrazole Derivatives 2006.
Strah-Pleynet; "5-HT2A Receptor Inverse-Agonists: Design and Structure-Activity Relationship of Novel Pyrazole Derivatives" 2005 ACS, 231st ACS National Meeting, MEDI 145.
Strah-Pleynet; "Bioisosteric Modifications of Urea Derivatives as 5HT2A Inverse-Agonists" 2005 ACS.
Street et al., "Olanzapine Treatment of Psychotic and Behavioral Symptoms in Patients With Alzheimer Disease in Nursing Care Facilities: a Double-Blind, Randomized, Placebo-Controlled Trial. The HGEU Study Group.," Arch Gen Psychiatry. Oct. 2000;57(10):968-76.
Takahashi et al., "Sarpogrelate Hydrochloride, a Serotonin2A Receptor Antagonist, Reduces Albuminuria in Diabetic Patients with Early-Stage Diabetic Nephropathy," Diabetes Res Clin Pract. Nov. 2002;58(2):123-9.
Takenaka et al., "The Effect of Anplag (Sarpogrelate HCl), Novel Selective 5-HT$_2$ Antagonist on Intraocular Pressure in Glaucoma Patients," Investig Ophthalmol Vis Sci, 36(4): S734 (1995).
Talvik-Lofti et al., "High 5HT2A Receptor Occupancy in Ml00907-Treated Schizophrenic Patients," Phychopharmacology (2000) 148:400-403.
Teegarden et al., "Discovery of 1-[3-(4-Bromo-2-methyl-2H-pyrazol-3-yl)-4-methoxyphenyl]- 3-(2,4-difluorophenyl)urea (Nelotanserin) and Related 5-Hydroxytryptamine 2A Inverse Agonists for the Treatment of Insomnia", *J Med. Chem.* 2003, vol. 53, DD. 1923-1936.
Teegarden et al; "5HT2A Inverse-Agonists for the Treatment of Insomnia" CTMC, pp. 1-28 (2008).
Teegarden et al; "Discovery of 1-[3-(4-Bromo-2-methyl-2H-pyrazol-3-yl)-4-methoxy-phenyl]- 3-(2,4-difluoro-phenyl)-urea (APD125) and Related 5-HT2A Inverse Agonists for the Treatment of Insomnia" *J Med. Chem.*; DD. 1-50 (2009).
*The International Classification of Sleep Disorders, Revised Diagnostic and Coding Manual*, American Academy of Sleep Medicine (2001) pp. 1-336 (also includes table of contents and glossary).
Vacante et al., Virology, 170: 353-361, (1989).
Van Zwieten, PA, "Receptors Involved in the Regulation of Vascular Tone," *Arzneimittelforschung*. 1985, vol. 35(12A): 1904-9.
Verstraete, M., "Prevention of Atherosclerotic Complications: Controlled Trial of Ketanserin," British Medical Journal, 1989, vol. 298, 424-30.
Vikenes, K. et al., "Serotonin is Associated with Coronary Artery Disease and Cardiac Events," *Circulation*, 1999, vol. 100, 483-9.
Vippagunta, S. et al., "Crystalline Solids,"*Advanced Drug Delivery Reviews*, 48:3-26 (2001).
White, E., "Deamination of Amines. 2-Phenylethyl Benzoate Via the Nitrosoamide Decomposition," *Org;. Syn. Coll.*, 1973, vol. 5, 336-339.
Wikstrom, H. et al., "Synthesis and Pharmacological Testing of 1, 2, 3, 4, 10, 14b-Hexahydro-6-methoxv . . . ,"*J Med. Chem.*, 2002, vol. 45, 3280-3285.
Wilson et al., "LY53857, a T2 receptor Antagonist, Delays Occlusion and Inhibits Platelet Aggregation in a Rabbit Model of Carotid Artery Occlusion," Thromb Haemost. Sep. 2, 1991; 66(3):355-60.
Winokur et al., "Acute Effects of Mirtazapine on Sleep Continuity and Sleep Architecture in Depressed Patients: a Pilot Study," Biol Psychiatry, Jul. 1, 2000;48(1):75-8.
Xiong et al; "Discovery and SAR of Highly Selective 5-HT2A Receptor Subtype Inverse-Agonists for Inhibition of Platelet Aggregation" 2008 ACS, 235th National Meeting, MEDI 45 (poster).
Xiong et al; "Synthesis and in Vivo Evaluation of Phenethylpiperazine Amides: Selective 5-Hydroxytryptamine2A

(56) References Cited

OTHER PUBLICATIONS

Receptor Antagonists for the Treatment of Insomnia", Journal of Medical Chemistry, vol. 53, 5696-5706 (2010).
Yamada, et al., Clin. Diagn. Virol. 1: 245-256 (1993).
Yamashita, T. et al., Haemostasis 30: 321-332 (2000).
Zhu et al., "Synthesis and Mode of Action of $^{123}$I- and $^3$H-labeled Thieno [2,3-c]pyridine Antagonists of Cell Adhesion Molecule Expression," *J Org;. Chem.* (2002) 67;943-948.
American Statistical and Diagnostic Handbook.
Bioreversible Carriers in Drug Design, ed. Edward B. Roche (1987).
Greene et al., Protecting Groups in Organic Synthesis, 3rd Edition, 1999 (Wiley).
Higuchi et al., "Pro-Drugs as a Novel Delivery Systems," vol. 14 of the ACS Symposium Series; and in Bioreversible Carriers in Drug Design, ed. Edward B. Roche, American Pharmaceutical Association and Pergamon Press, 1987.
Remington, The Science and Practice of Pharmacy, 20[1] Edition, 2000 (Lippincott Williams & Wilkins).
Database Beilstein [Online] Beilstein Institute for Organic Chemistry, Frankfurt-Main, DE; XP002535545 Database Accession No. 5926580 (BRN) the whole document.
Gottlieb et al., "NMR Chemical Shifts of Common Laboratory Solvents as Trace Impurities," J. Org. Chem., 1997, 62(21): 7512-7515.
Griesser, "The Importance of Solvates, , in Polymorphism in the Pharmaceutical Industry," 211-233; Rolf Hilfiker, ed., 2006.
Grotewiel et al., "Receptors Exhibit Constitutive Activity that is Blocked by Inverse Agonists," Faseb J., Abstract 353, 8(7), May 21-25, 1994 (1 page).
International Preliminary Report on Patentability; PCT/US2007/021182; P. Lauro; Nov. 4, 2008.
International Search Report and Written Opinion; PCT/US2009/002019; P. Ipinazar; Apr. 1, 2009.
Jeon et al., "The synthesis of a new pyrazolylimidazolinone via 1,3-dipolar cycloaddition reaction of N-methyl sydnone with methyl propiolate," Bull. Korean Chem. Soc., 1998, 19(7): 725-726, XP002535544.
Storey et al., "Automation of Solid Form Screening Procedures in the Pharmaceutical Industry—How to Avoid the Bottlenecks," Crystallography Reviews, 2004, 10(1): 45-56.
Vasilevsky et al., "Study of the Heterocyclization of vic-Substituted Hydrazides of Acetylenylpyrazolecalboxylic Acids into N-Amino Pyrazolopyridinones," J. Hetercycl. Chem., 2002, 39: 1229-1233.
Vasilevskii, "Oxidative Iodination of Substituted N-Methylpyrazoles," Bull. Acad. Sci. USSR vol. 29, No. 5, 1980, pp. 778-784, XP002535543.
Written Opinion; PCT/US2004/023488; A. Zellner; Jul. 22, 2003.

* cited by examiner

PROCESSES FOR THE PREPARATION OF PYRAZOLE DERIVATIVES USEFUL AS MODULATORS OF THE 5-HT2A SEROTONIN RECEPTOR

CROSS REFERENCE TO RELATED APPLICATIONS

This application is continuation of U.S. National Phase Application 12/936,038, filed Oct.1, 2010, which is a §371 National Stage Application of International Application PCT/US09/02019, filed Apr.1, 2009, which claims the benefit of priority of U.S. Provisional Appl. No.61/072,697, filed Apr.2, 2008, each of which is incorporated herein by reference in its entirety.

FIELD OF THE INVENTION

The present invention relates to processes for preparing pyrazole derivatives of Formula (I) and salts and pharmaceutical compositions of the salts thereof, useful as modulators of 5-$HT_{2A}$ serotonin receptor activity. The present invention also relates to intermediates used in the processes, and their preparation. The present invention also relates to salts of compounds of Formula (I) and pharmaceutical compositions thereof.

BACKGROUND OF THE INVENTION

Receptors for serotonin (5-hydroxytryptamine, 5-HT) are an important class of G protein coupled receptors. Serotonin receptors are divided into seven subfamilies, referred to as 5-$HT_1$ through 5-$HT_7$, inclusive. These subfamilies are further divided into subtypes. For example, the 5-$HT_2$ subfamily is divided into three receptor subtypes: 5-$HT_{2A}$, 5-$HT_{2B}$, and 5-$HT_{2C}$. Certain pyrazole derivatives are modulators of 5-$HT_{2A}$ serotonin receptor activity useful in the treatment of insomnia and related sleep disorders, platelet aggregation, coronary artery disease, myocardial infarction, transient ischemic attack, angina, stroke, atrial fibrillation, reducing the risk of blood clot formation, asthma or symptoms thereof, agitation or symptoms thereof, behavioral disorders, drug induced psychosis, excitative psychosis, Gilles de la Tourette's syndrome, manic disorder, organic or NOS psychosis, psychotic disorders, psychosis, acute schizophrenia, chronic schizophrenia, NOS schizophrenia and related disorders, diabetic-related disorders, progressive multifocal leukoencephalopathy and the like.

SUMMARY OF THE INVENTION

One aspect of the present invention pertains to processes for preparing compounds of Formula (I):

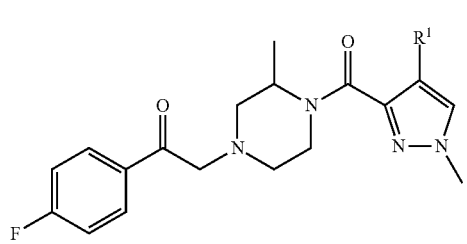

(I)

or a salt thereof, wherein:
$R^1$ is halogen;

comprising reacting a compound of Formula (II):

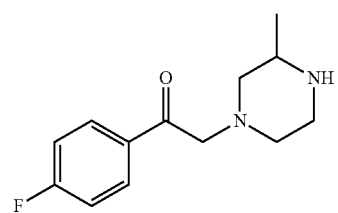

(II)

or a salt thereof, with a compound of Formula (III):

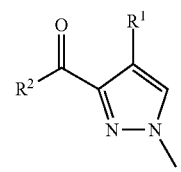

(III)

or a salt thereof, wherein:
$R^2$ is a leaving group;
to form a compound of Formula (I) or a salt thereof.

One aspect of the present invention pertains to processes for preparing compounds of Formula (II) or a salt thereof, comprising reacting a compound of Formula (IV):

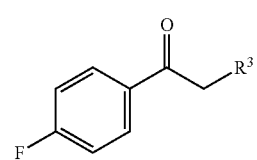

(IV)

wherein:
$R^3$ is halogen, $C_1$-$C_6$ alkylsulfonyloxy or arylsulfonyloxy; wherein said arylsulfonyloxy may be further substituted with $C_1$-$C_6$ alkyl;
with a compound of Formula (V):

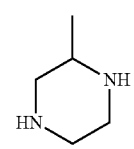

(V)

or a salt thereof, to form a compound of Formula (II) or a salt thereof.

One aspect of the present invention pertains to processes for preparing compounds of Formula (III) or a salt thereof, comprising reacting a compound of Formula (VI):

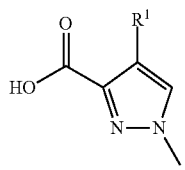

(VI)

or a salt thereof, with a compound of Formula (VII):

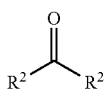

(VII)

or a salt thereof, to form a compound of Formula (III) or a salt thereof.

The present invention further provides processes for preparing compounds of Formula (I) or a salt thereof, comprising the steps:

(a) reacting a compound of Formula (VI) or a salt thereof, with a compound of Formula (VII) or a salt thereof, wherein to form a compound of Formula (III) or a salt thereof; and (b) further reacting the compound of Formula (III) or a salt thereof in situ with a compound of Formula (II) or a salt thereof, to form a compound of Formula (I) or a salt thereof.

One aspect of the present invention pertains to processes for preparing salts of compounds of Formula (I):

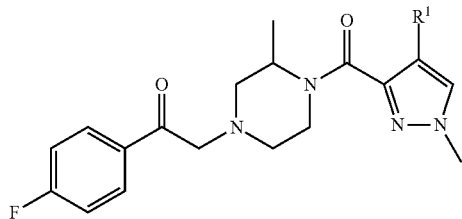

(I)

comprising reacting a compound of Formula (I) with a salt-forming acid to form a salt of a compound of Formula (I).

One aspect of the present invention pertains to hydrochloride salts of compounds of Formula (I) prepared by the processes described herein.

In some embodiments the present invention provides (S)-2-(4-(4-chloro-1-methyl-1H-pyrazole-3-carbonyl)-3-methylpiperazin-1-yl)-1-(4-fluorophenyl)ethanone hydrochloride, represented by the following structure:

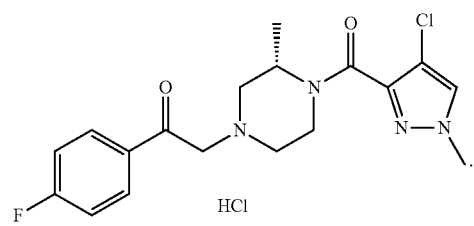 [SMILES: C[C@H]1CN(CC(=O)c2ccc(F)cc2)CCN1C(=O)c1nn(C)cc1Cl ; Cl]

In some embodiments the present invention provides (R)-2-(4-(4-chloro-1-methyl-1H-pyrazole-3-carbonyl)-3-methylpiperazin-1-yl)-1-(4-fluorophenyl)ethanone hydrochloride, represented by the following structure:

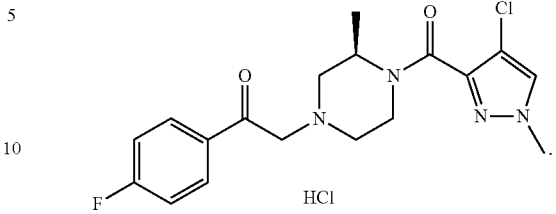

In some embodiments the present invention provides (S)-2-(4-(4-bromo-1-methyl-1H-pyrazole-3-carbonyl)-3-methylpiperazin-1-yl)-1-(4-fluorophenyl)ethanone hydrochloride, represented by the following structure:

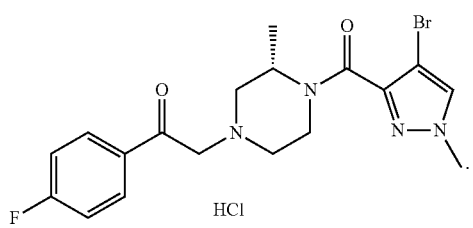

In some embodiments the present invention provides (R)-2-(4-(4-bromo-1-methyl-1H-pyrazole-3-carbonyl)-3-methylpiperazin-1-yl)-1-(4-fluorophenyl)ethanone hydrochloride, represented by the following structure:

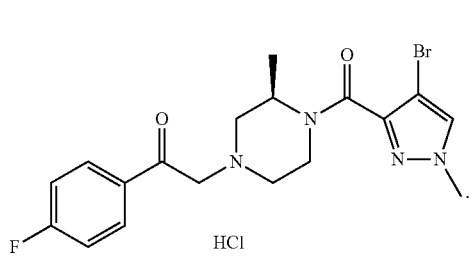 [SMILES: C[C@@H]1CN(CC(=O)c2ccc(F)cc2)CCN1C(=O)c1nn(C)cc1Br ; Cl]

One aspect of the present invention pertains to pharmaceutical compositions comprising compounds of Formula (I) prepared by the processes described herein.

One aspect of the present invention pertains to pharmaceutical compositions comprising a hydrochloride salt of a compound of Formula (I) and a pharmaceutically acceptable carrier.

One aspect of the present invention pertains to methods for treating a 5-HT$_{2A}$ mediated disorder in an individual comprising administering to the individual in need thereof a therapeutically effective amount of a hydrochloride salt as described herein.

One aspect of the present invention pertains to methods for treating coronary artery disease, myocardial infarction, transient ischemic attack, angina, stroke, and atrial fibrillation in an individual comprising administering to the individual in need thereof a therapeutically effective amount of a hydrochloride salt as described herein.

One aspect of the present invention pertains to methods for treating a sleep disorder in an individual comprising administering to the individual in need thereof a therapeutically effective amount of a hydrochloride salt as described herein.

One aspect of the present invention pertains to methods for treating a dyssomnia in an individual comprising administering to the individual in need thereof a therapeutically effective amount of a hydrochloride salt as described herein.

One aspect of the present invention pertains to methods for treating insomnia in an individual comprising administering to the individual in need thereof a therapeutically effective amount of a hydrochloride salt as described herein.

One aspect of the present invention pertains to methods for treating a parasomnia in an individual comprising administering to the individual in need thereof a therapeutically effective amount of a hydrochloride salt as described herein.

One aspect of the present invention pertains to methods for increasing slow wave sleep in an individual comprising administering to the individual in need thereof a therapeutically effective amount of a hydrochloride salt as described herein.

One aspect of the present invention pertains to methods for improving sleep consolidation in an individual comprising administering to the individual in need thereof a therapeutically effective amount of a hydrochloride salt as described herein.

One aspect of the present invention pertains to methods for improving sleep maintenance in an individual comprising administering to the individual in need thereof a therapeutically effective amount of a hydrochloride salt as described herein.

One aspect of the present invention pertains to methods for treating a sleep disorder selected from: a dyssomnia, insomnia or a parasomnia; or for increasing slow wave sleep, improving sleep consolidation or improving sleep maintenance in an individual comprising administering to said individual in need thereof a therapeutically effective amount of the hydrochloride salt as described herein.

One aspect of the present invention pertains to methods for treating a condition associated with platelet aggregation in an individual comprising administering to the individual in need thereof a therapeutically effective amount of a hydrochloride salt as described herein.

One aspect of the present invention pertains to methods for reducing the risk of blood clot formation in an individual comprising administering to the individual in need thereof a therapeutically effective amount of a hydrochloride salt as described herein.

One aspect of the present invention pertains to methods for reducing the risk of blood clot formation in an angioplasty or coronary bypass surgery individual comprising administering to the individual in need thereof a therapeutically effective amount of a hydrochloride salt as described herein.

One aspect of the present invention pertains to methods for reducing the risk of blood clot formation in an individual suffering from atrial fibrillation, comprising administering to the individual in need thereof a therapeutically effective amount of a hydrochloride salt as described herein.

One aspect of the present invention pertains to methods for treating a diabetic-related disorder in an individual suffering from atrial fibrillation, comprising administering to the individual in need thereof a therapeutically effective amount of a hydrochloride salt as described herein.

One aspect of the present invention pertains to methods for treating progressive multifocal leukoencephalopathy in an individual suffering from atrial fibrillation, comprising administering to the individual in need thereof a therapeutically effective amount of a hydrochloride salt as described herein.

One aspect of the present invention pertains to methods for treating hypertension in an individual suffering from atrial fibrillation, comprising administering to the individual in need thereof a therapeutically effective amount of a hydrochloride salt as described herein.

One aspect of the present invention pertains to methods for treating pain in an individual suffering from atrial fibrillation, comprising administering to the individual in need thereof a therapeutically effective amount of a hydrochloride salt as described herein.

One aspect of the present invention pertains to use of hydrochloride salts as described herein for the manufacture of a medicament for the treatment of a sleep disorder.

One aspect of the present invention pertains to use of hydrochloride salts as described herein for the manufacture of a medicament for the treatment of a dyssomnia.

One aspect of the present invention pertains to use of hydrochloride salts as described herein for the manufacture of a medicament for the treatment of insomnia.

One aspect of the present invention pertains to use of hydrochloride salts as described herein for the manufacture of a medicament for the treatment of a parasomnia.

One aspect of the present invention pertains to use of hydrochloride salts as described herein for the manufacture of a medicament for increasing slow wave sleep.

One aspect of the present invention pertains to use of hydrochloride salts as described herein for the manufacture of a medicament for improving sleep consolidation.

One aspect of the present invention pertains to use of hydrochloride salts as described herein for the manufacture of a medicament for improving sleep maintenance.

One aspect of the present invention pertains to use of hydrochloride salts as described herein for the manufacture of a medicament for the treatment of a sleep disorder selected from: a dyssomnia, insomnia or a parasomnia; or for the manufacture of a medicament for increasing slow wave sleep, improving sleep consolidation or improving sleep maintenance.

One aspect of the present invention pertains to use of hydrochloride salts as described herein for the manufacture of a medicament for the treatment of a 5-$HT_{2A}$ mediated disorder.

One aspect of the present invention pertains to use of hydrochloride salts as described herein for the manufacture of a medicament for the treatment of a 5-$HT_{2A}$ mediated disorder selected from the group consisting of coronary artery disease, myocardial infarction, transient ischemic attack, angina, stroke, and atrial fibrillation.

One aspect of the present invention pertains to use of hydrochloride salts as described herein for the manufacture of a medicament for the treatment of a condition associated with platelet aggregation.

One aspect of the present invention pertains to use of hydrochloride salts as described herein for the manufacture of a medicament for the reduction of the risk of blood clot formation.

One aspect of the present invention pertains to use of hydrochloride salts as described herein for the manufacture of a medicament for the reduction of the risk of blood clot formation in an angioplasty or coronary bypass surgery individual.

One aspect of the present invention pertains to use of hydrochloride salts as described herein for the manufacture of a medicament for the reduction of the risk of blood clot formation in an individual suffering from atrial fibrillation.

One aspect of the present invention pertains to use of hydrochloride salts as described herein for the manufacture of a medicament for the treatment of a diabetic-related disorder.

One aspect of the present invention pertains to use of hydrochloride salts as described herein for the manufacture of a medicament for the treatment of progressive multifocal leukoencephalopathy.

One aspect of the present invention pertains to use of hydrochloride salts as described herein for the manufacture of a medicament for the treatment of hypertension.

One aspect of the present invention pertains to use of a hydrochloride salt as described herein for the manufacture of a medicament for the treatment of pain.

One aspect of the present invention pertains to hydrochloride salts as described herein for use in a method of treatment of the human or animal body by therapy.

One aspect of the present invention pertains to hydrochloride salts as described herein for use in a method of treatment of a 5-HT$_{2A}$ mediated disorder.

One aspect of the present invention pertains to hydrochloride salts as described herein for use in a method of treatment of a 5-HT$_{2A}$ mediated disorder selected from the group consisting of coronary artery disease, myocardial infarction, transient ischemic attack, angina, stroke, and atrial fibrillation.

One aspect of the present invention pertains to hydrochloride salts as described herein for use in a method of treatment of a sleep disorder.

One aspect of the present invention pertains to hydrochloride salts as described herein for use in a method of treatment of a dyssomnia.

One aspect of the present invention pertains to hydrochloride salts as described herein for use in a method of treatment of insomnia.

One aspect of the present invention pertains to hydrochloride salts as described herein for use in a method of treatment of a parasomnia.

One aspect of the present invention pertains to hydrochloride salts as described herein for use in a method for increasing slow wave sleep.

One aspect of the present invention pertains to hydrochloride salts as described herein for use in a method for improving sleep consolidation.

One aspect of the present invention pertains to hydrochloride salts as described herein for use in a method for improving sleep maintenance.

One aspect of the present invention pertains to hydrochloride salts as described herein for use in a method of treatment of a sleep disorder selected from: a dyssomnia, insomnia or a parasomnia; or for use in a method for increasing slow wave sleep, improving sleep consolidation or improving sleep maintenance.

One aspect of the present invention pertains to hydrochloride salts as described herein for use in a method of treatment of a condition associated with platelet aggregation.

One aspect of the present invention pertains to hydrochloride salts as described herein for use in a method of reducing the risk of blood clot formation.

One aspect of the present invention pertains to hydrochloride salts as described herein for use in a method of reducing the risk of blood clot formation in an angioplasty or coronary bypass surgery individual.

One aspect of the present invention pertains to hydrochloride salts as described herein for use in a method of reducing the risk of blood clot formation in an individual suffering from atrial fibrillation.

One aspect of the present invention pertains to hydrochloride salts as described herein for use in a method of treatment of a diabetic-related disorder.

One aspect of the present invention pertains to hydrochloride salts as described herein for use in a method of treatment of progressive multifocal leukoencephalopathy.

One aspect of the present invention pertains to hydrochloride salts as described herein for use in a method of treatment of hypertension.

One aspect of the present invention pertains to hydrochloride salts as described herein for use in a method of treatment of pain.

One aspect of the present invention pertains to processes for preparing a composition comprising admixing a hydrochloride salt as described herein and a pharmaceutically acceptable carrier.

One aspect of the present invention pertains to hydrobromide salts of a compound of Formula (II) prepared by the processes described herein.

One aspect of the present invention pertains to compounds of Formula (III):

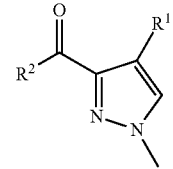

(III)

and salts thereof, wherein:
R$^1$ is halogen; and
R$^2$ is 1H-imidazolyl;
prepared by the processes described herein.

DETAILED DESCRIPTION

Definitions

For clarity and consistency, the following definitions will be used throughout this patent document.

The term "agonists" is intended to mean moieties that interact and activate the receptor, such as the 5-HT$_{2A}$ serotonin receptor, and initiate a physiological or pharmacological response characteristic of that receptor. For example, when moieties activate the intracellular response upon binding to the receptor, or enhance GTP binding to membranes.

The term "antagonists" is intended to mean moieties that competitively bind to the receptor at the same site as agonists (for example, the endogenous ligand), but which do not activate the intracellular response initiated by the active form of the receptor, and can thereby inhibit the intracellular responses by agonists or partial agonists. Antagonists do not diminish the baseline intracellular response in the absence of an agonist or partial agonist.

The term "hydrate" as used herein means a salt of the invention that further includes a stoichiometric or non-stoichiometric amount of water bound by non-covalent intermolecular forces.

The term "in need of treatment" and the term "in need thereof" when referring to treatment are used interchangeably to mean a judgment made by a caregiver (e.g. physician, nurse, nurse practitioner, etc. in the case of humans;

veterinarian in the case of animals, including non-human mammals) that an individual or animal requires or will benefit from treatment. This judgment is made based on a variety of factors that are in the realm of a caregiver's expertise, but that includes the knowledge that the individual or animal is ill, or will become ill, as the result of a disease, condition or disorder that is treatable by the salts of the invention. Accordingly, the salts of the invention can be used in a protective or preventive manner; or salts of the invention can be used to alleviate, inhibit or ameliorate the disease, condition or disorder.

The term "individual" is intended to mean any animal, including mammals, preferably mice, rats, other rodents, rabbits, dogs, cats, swine, cattle, sheep, horses, or primates, and most preferably humans.

The term "inverse agonists" is intended to mean moieties that bind to the endogenous form of the receptor or to the constitutively activated form of the receptor, and which inhibit the baseline intracellular response initiated by the active form of the receptor below the normal base level of activity which is observed in the absence of agonists or partial agonists, or decrease GTP binding to membranes. Preferably, the baseline intracellular response is inhibited in the presence of the inverse agonist by at least 30%, more preferably by at least 50%, and most preferably by at least 75%, as compared with the baseline response in the absence of the inverse agonist.

The term "pharmaceutical composition" is intended to mean a composition comprising at least one active ingredient; including but not limited to salts of the present invention and solvates and hydrates thereof; whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

The term "solvate" as used herein means a salt of the invention that further includes a stoichiometric or non-stoichiometric amount of a solvent bound by non-covalent intermolecular forces. Preferred solvents are volatile, non-toxic, and/or acceptable for administration to humans in trace amounts.

The term "substituted" as used herein indicates that at least one hydrogen atom of the chemical group is replaced by a non-hydrogen substituent or group, the non-hydrogen substituent or group can be monovalent or divalent. When the substituent or group is divalent, then it is understood that this group is further substituted with another substituent or group. When a chemical group herein is "substituted" it may have up to the full valance of substitution; for example, a methyl group can be substituted by 1, 2, or 3 substituents, a methylene group can be substituted by 1 or 2 substituents, a phenyl group can be substituted by 1, 2, 3, 4, or 5 substituents, a naphthyl group can be substituted by 1, 2, 3, 4, 5, 6, or 7 substituents and the like.

The term "therapeutically effective amount" is intended to mean the amount of active salt or pharmaceutical agent that elicits the biological or medicinal response in a tissue, system, animal, individual or human that is being sought by a researcher, veterinarian, medical doctor or other clinician or caregiver; or by an individual, which includes one or more of the following:

(1) Preventing the disease, for example, preventing a disease, condition or disorder in an individual that may be predisposed to the disease, condition or disorder but does not yet experience or display the pathology or symptomatology of the disease;

(2) Inhibiting the disease, for example, inhibiting a disease, condition or disorder in an individual that is experiencing or displaying the pathology or symptomatology of the disease, condition or disorder (i.e., arresting further development of the pathology and/or symptomatology); and (3) Ameliorating the disease, for example, ameliorating a disease, condition or disorder in an individual that is experiencing or displaying the pathology or symptomatology of the disease, condition or disorder (i.e., reversing the pathology and/or symptomatology).

Chemical Group, Moiety or Radical

The term "$C_1$-$C_6$ acyl" refers to a $C_{1-6}$ alkyl radical attached directly to the carbon of a carbonyl group wherein the definition for alkyl is as described herein; some examples include, but are not limited to, acetyl, propionyl, n-butanoyl, isobutanoyl, pivaloyl, pentanoyl and the like.

The term "$C_1$-$C_6$ acyloxy" refers to an acyl radical attached directly to an oxygen atom [—OC(=O)—$C_1$-$C_6$ alkyl] wherein acyl has the same definition has described herein; some examples include but are not limited to acetyloxy [—OC(=O)$CH_3$], propionyloxy, butanoyloxy, isobutanoyloxy, pivaloyloxy and the like.

The term "$C_1$-$C_6$ alkoxy" is intended to mean a $C_1$-$C_6$ alkyl radical, as defined herein, attached directly to an oxygen atom. Some embodiments are 1 to 5 carbons; some embodiments are 1 to 4 carbons; some embodiments are 1 to 3 carbons; and some embodiments are 1 or 2 carbons. Examples include methoxy, ethoxy, n-propoxy, isopropoxy, n-butoxy, t-butoxy, isobutoxy, sec-butoxy and the like.

The term "$C_1$-$C_6$ alkyl" is intended to mean a straight or branched carbon radical containing 1 to 6 carbons. Some embodiments are 1 to 5 carbons. Some embodiments are 1 to 4 carbons. Some embodiments are 1 to 3 carbons. Some embodiments are 1 or 2 carbons. Some embodiments are 1 carbon. Examples of an alkyl include, but are not limited to, methyl, ethyl, n-propyl, isopropyl, n-butyl, sec-butyl, isobutyl, t-butyl, pentyl, isopentyl, t-pentyl, neo-pentyl, 1-methylbutyl [i.e., —CH($CH_3$)$CH_2CH_2CH_3$], 2-methylbutyl [i.e., —$CH_2$CH($CH_3$)$CH_2CH_3$], n-hexyl and the like.

The term "$C_1$-$C_6$ alkylsulfonyloxy" is intended to mean the group shown below wherein $C_1$-$C_6$ alkyl has the same definition as used herein:

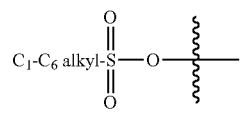

Examples of $C_1$-$C_6$ alkylsulfonyloxy include, but are not limited to, methylsulfonyloxy, ethylsulfonyloxy and the like.

The term "$C_1$-$C_6$ arylsulfonyloxy" is intended to mean the group shown below wherein $C_1$-$C_6$ alkyl has the same definition as used herein:

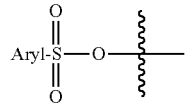

Examples of arylsulfonyloxy include but are not limited to phenylsulfonyloxy naphthylsulfonyloxy and the like.

The term "halogen" or "halo" is intended to mean to a fluoro, chloro, bromo or iodo group.

The term "heteroaryl" is intended to mean an aromatic ring system that may be a single ring, two fused rings or three fused rings wherein at least one ring atom is a heteroatom selected from, but not limited to, the group consisting of O, S and N. Examples of heteroaryl groups include, but are not limited to, pyridyl, benzofuranyl, pyrazinyl, pyridazinyl, pyrimidinyl, triazinyl, quinolinyl, benzoxazolyl, benzothiazolyl, 1H-benzimidazolyl, isoquinolinyl, quinazolinyl, quinoxalinyl, and the like. In some embodiments, the heteroaryl group contains a heteroatom selected from, for example, the group consisting of O, S and N, wherein N is substituted with H (i.e., NH). Examples include, but are not limited to, pyrrolyl, indolyl, 1H-benzoimidazol-2-yl, 1H-benzo[d][1,2,3]triazol-1-yl and the like.

The term "heterocyclyl" or "heterocyclic" is intended to mean a ring system containing 3 to 15 ring atoms that may be a single ring, two fused rings or three fused rings, wherein at least one ring atom is a heteroatom or substituted heteroatom selected from, but not limited to, the group consisting of O, S, S(=O), S(=O)$_2$ and NH. In some embodiments, the ring carbon atoms are optionally substituted with oxo thus forming a carbonyl group. In some embodiments the heterocyclic group is a 3-, 4-, 5-, 6- or 7-membered ring. In some embodiments the heterocyclic group is a bicyclic group in which any of the above-defined heterocyclic rings is fused to a benzene ring. In some embodiments the heterocyclic group is a tricyclic group in which any of the above-defined heterocyclic rings is fused to two benzene rings. Examples of a heterocyclic group include, but are not limited to: [1,4]-oxazepanyl, 10,11-dihydro-5H-dibenzo[b,f]azepinyl, azepanyl, azetidinyl, aziridinyl, imidazolidinyl, imidazolinyl, indolinyl, morpholinyl, piperidinyl, piperazinyl, pyrazolidinyl, pyrazolinyl, pyrrolidinyl, pyrrolinyl, succinimidyl, thiomorpholinyl, and the like. In some embodiments a heterocyclic group can be bonded only at a ring carbon or ring nitrogen as allowed by the respective formulae unless otherwise specified. In some embodiments a heterocyclic group can be bonded only at a ring nitrogen as allowed by the respective formulae unless otherwise specified.

The term "heteroaryloxy" is intended to mean an oxygen radical further substituted with a heteroaryl group as defined herein.

The term "heterocyclyloxy" is intended to mean an oxygen radical further substituted with a heterocyclic group as defined herein.

The term "leaving group" is a term well known to the skilled chemist, examples being halogens such as chloro, bromo and iodo; $C_1$-$C_6$ acyloxy groups such as acetyloxy, pivaloyloxy and the like; $C_1$-$C_6$alkoxy groups such as methoxy, ethoxy, isopropoxy and the like; N-linked heteroaryl groups such as 1H-imidazol-1-yl and the like; heteroaryloxy groups such as 1H-benzo[d][1,2,3]triazol-1-yloxy and the like; and heterocyclyloxy groups such as 2,5-dioxopyrrolidin-1-yloxy and the like. In some embodiments, the term leaving group is intended to mean a leaving group other than chloro. In some embodiments, the term leaving group is intended to mean a leaving group other than 3H-[1,2,3]triazolo[4,5-b]pyridin-3-yloxy. In some embodiments, the term leaving group is intended to mean a leaving group other than the leaving group formed upon activation of a carboxylic acid with 1-propylphosphonic anhydride.

The term "N-linked heteroaryl" is intended to mean monocyclic and polycyclic aromatic ring radicals having at least one nitrogen ring atom through which the ring radical is bonded. Examples of N-linked heteroaryl groups include but are not limited to 1H-imidazol-1-yl and the like.

Processes Of The Invention

The present invention is directed inter alia to processes and intermediates for the preparation of pyrazole derivatives that are useful as modulators of 5-HT$_{2A}$ serotonin receptor activity for the treatment of disorders associated with 5-HT$_{2A}$ serotonin receptor expression and/or activity such as, for example, insomnia and related sleep disorders, platelet aggregation, coronary artery disease, myocardial infarction, transient ischemic attack, angina, stroke, atrial fibrillation, reducing the risk of blood clot formation, asthma or symptoms thereof, agitation or symptoms thereof, behavioral disorders, drug induced psychosis, excitative psychosis, Gilles de la Tourette's syndrome, manic disorder, organic or NOS psychosis, psychotic disorders, psychosis, acute schizophrenia, chronic schizophrenia, NOS schizophrenia and related disorders, diabetic-related disorders, progressive multifocal leukoencephalopathy and the like. The present invention further provides processes for preparing pyrazole derivatives of Formula (I) and salts and pharmaceutical compositions thereof, and intermediates used in the processes and their preparation.

Example processes and intermediates of the present invention are provided below in Scheme I, wherein each constituent member of the compounds depicted are defined herein.

Scheme I

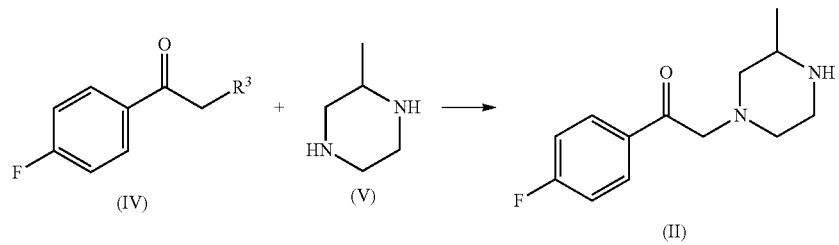

-continued

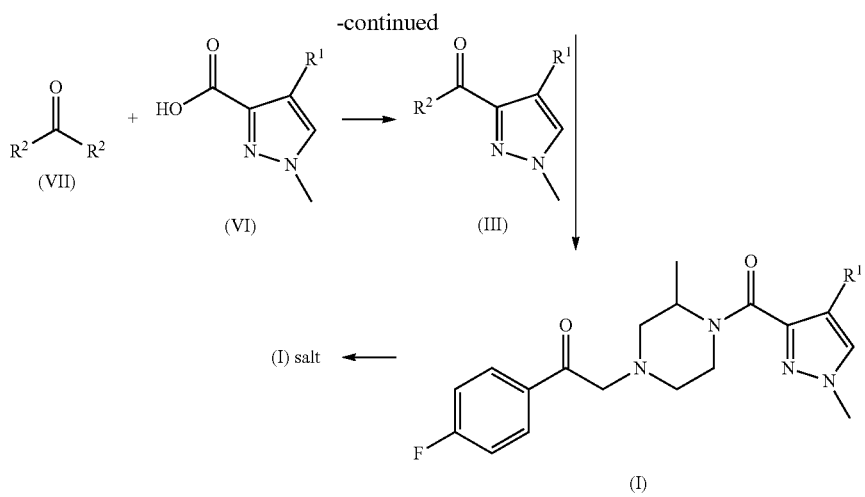

One aspect of the present invention pertains to processes, such as those exemplified by Scheme I (supra), that involve compounds of Formulae (I), (II), (III), (IV), (V), (VI) and (VII) or salts thereof, wherein:

$R^1$ is halogen;

$R^2$ is a leaving group; and $R^3$ is halogen, $C_1$-$C_6$ alkylsulfonyloxy or arylsulfonyloxy; wherein said arylsulfonyloxy may be further substituted with $C_1$-$C_6$ alkyl.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables ($R^1$, $R^2$ and $R^3$) contained within the generic chemical formulae described herein [(I), (II), (III), (IV), (V), (VI) and (VII)] are specifically embraced by the present invention just as if they were explicitly disclosed, to the extent that such combinations embrace compounds that result in stable compounds (i.e., compounds that can be isolated, characterized and tested for biological activity).

One aspect of the present invention pertains to a process for preparing a compound of Formula (I):

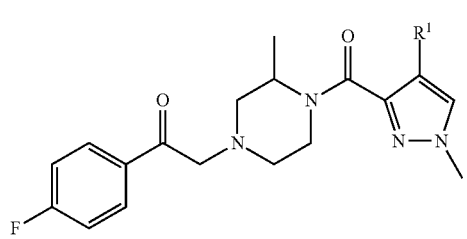
(I)

or a salt thereof, comprising:

(a) reacting a compound of Formula (VI):

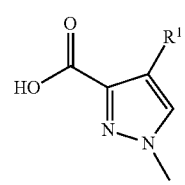
(VI)

or a salt thereof, with a compound of Formula (VII):

(VII)

or a salt thereof, to form a compound of Formula (III):

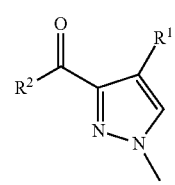
(III)

or a salt thereof;

(b) reacting a compound of Formula (IV):

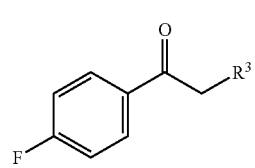
(IV)

with a compound of Formula (V):

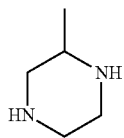

or a salt thereof, to form a compound of Formula (II):

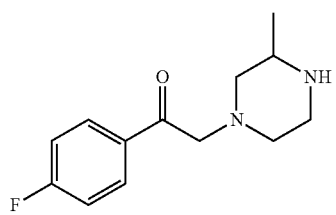

or a salt thereof; and (c) reacting the compound of Formula (II) or a salt thereof, with the compound of Formula (III) or a salt thereof, to form the compound of Formula (I) or a salt thereof; wherein:

$R^1$ is a halogen
$R^2$ is a leaving group; and
$R^3$ is a halogen.

The Group $R^1$:
In some embodiments, $R^1$ is halogen.
In some embodiments, $R^1$ is fluoro.
In some embodiments, $R^1$ is chloro.
In some embodiments, $R^1$ is bromo.
In some embodiments, $R^1$ is iodo.

The Group $R^2$:
In some embodiments, $R^2$ is a leaving group.
In some embodiments, $R^2$ is an N-linked heteroaryl.
In some embodiments, $R^2$ is 1H-imidazol-1-yl.
In some embodiments, $R^2$ is a leaving group other than chloro.
In some embodiments, $R^2$ is a leaving group other than 3H-[1,2,3]triazolo[4,5-b]pyridin-3-yloxy. It is understood that the leaving group 3H-[1,2,3]triazolo[4,5-b]pyridin-3-yloxy is the leaving group formed upon activation of a carboxylic acid with O-(7-azabenzotriazol-1-yl)-N,N,N',N'-tetramethyluronium hexafluorophosphate (HATU).
In some embodiments, $R^2$ is a leaving group other than the leaving group formed upon activation of a carboxylic acid with 1-propylphosphonic anhydride.

The Group $R^3$:
In some embodiments, $R^3$ is halogen.
In some embodiments, $R^3$ is fluoro.
In some embodiments, $R^3$ is chloro.
In some embodiments, $R^3$ is bromo.
In some embodiments, $R^3$ is iodo.
In some embodiments, $R^3$ is $C_1$-$C_6$ alkylsulfonyloxy.
In some embodiments, $R^3$ is methylsulfonyloxy.
In some embodiments, $R^3$ is arylsulfonyloxy.
In some embodiments, $R^3$ is phenylsulfonyloxy.
In some embodiments, $R^3$ is arylsulfonyloxy further substituted with $C_1$-$C_6$ alkyl.
In some embodiments, $R^3$ is tosyloxy.

Certain Combinations of the Present Invention:
In some embodiments:
$R^1$ is chloro;
$R^2$ is 1H-imidazol-1-yl; and
$R^3$ is bromo.
In some embodiments:
$R^1$ is bromo;
$R^2$ is 1H-imidazol-1-yl; and
$R^3$ is bromo.

Amide-Forming Step

One aspect of the present invention pertains to processes for preparing compounds of Formula (I):

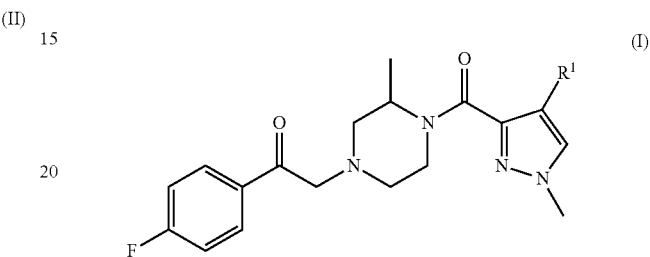

or a salt thereof, comprising reacting a compound of Formula (II):

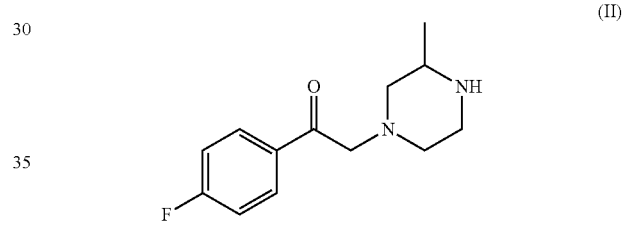

or a salt thereof, with a compound of Formula (III):

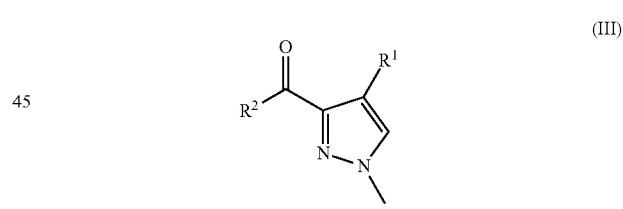

or a salt thereof, to form a compound of Formula (I) or a salt thereof.

In some embodiments, the compound of Formula (I) is the R enantiomer.
In some embodiments, the compound of Formula (I) is the S enantiomer.
In some embodiments, the compound of Formula (I) is selected from: the R enantiomer, the S enantiomer or a mixture thereof.
In some embodiments, the process comprises reacting a hydrobromide salt of a compound of Formula (II) with a compound of Formula (III) or a salt thereof to form a compound of Formula (I) or a salt thereof.
In some embodiments, the process comprises reacting a hydrochloride salt of a compound of Formula (II) with a compound of Formula (III) or a salt thereof to form a compound of Formula (I) or a salt thereof.

In some embodiments, R¹ is chloro.
In some embodiments, R¹ is bromo.
In some embodiments, R² is an N-linked heteroaryl.
In some embodiments, R² is 1H-imidazol-1-yl.
In some embodiments, R¹ is chloro and R² is 1H-imidazol-1-yl.

In some embodiments, the reacting a compound of Formula (II) or a salt thereof, with a compound of Formula (III) or a salt thereof is carried out in the presence of a base.

In some embodiments, the reacting a compound of Formula (II) or a salt thereof, with a compound of Formula (III) or a salt thereof is carried out in the presence of a tertiary amine.

In some embodiments, the reacting a compound of Formula (II) or a salt thereof, with a compound of Formula (III) or a salt thereof is carried out in the presence of triethylamine.

In some embodiments, the reacting a compound of Formula (II) or a salt thereof, with a compound of Formula (III) or a salt thereof is carried out in the presence of a catalyst.

In some embodiments, the reacting a compound of Formula (II) or a salt thereof, with a compound of Formula (III) or a salt thereof is carried out in the presence of 2-hydroxypyridine.

In some embodiments, the reacting a compound of Formula (II) or a salt thereof, with a compound of Formula (III) or a salt thereof is carried out in the presence of N,N-dimethylaminopyridine.

In some embodiments, the reacting a compound of Formula (U) or a salt thereof, with a compound of Formula (III) or a salt thereof is carried out at a temperature of about 20° C. to about reflux temperature.

In some embodiments, the reacting a compound of Formula (II) or a salt thereof, with a compound of Formula (III) or a salt thereof is carried out at a temperature of about 40° C. to about reflux temperature.

In some embodiments, the reacting a compound of Formula (II) or a salt thereof, with a compound of Formula (III) or a salt thereof is carried out at a temperature of about 60° C. to about 80° C.

In some embodiments, the reacting a compound of Formula (II) or a salt thereof, with a compound of Formula (III) or a salt thereof is carried out in an amide-forming solvent.

In some embodiments, the reacting a compound of Formula (II) or a salt thereof, with a compound of Formula (III) or a salt thereof is carried out in an aprotic solvent.

In some embodiments, the reacting a compound of Formula (II) or a salt thereof, with a compound of Formula (III) or a salt thereof is carried out in acetonitrile.

In some embodiments, the molar ratio of the compound of Formula (II) to the compound of Formula (III) is about 2:1 to about 0.5:1.

In some embodiments, the molar ratio of the compound of Formula (II) to the compound of Formula (III) is about 1:1.

Alkylation Step

One aspect of the present invention pertains to processes for preparing compounds of Formula (II) comprising reacting a compound of Formula (IV):

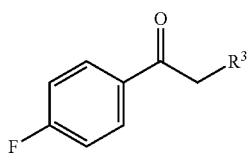

(IV)

with a compound of Formula (V):

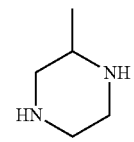

(V)

or a salt thereof, to form a compound of Formula (II) or a salt thereof.

In some embodiments, the process forms a hydrobromide salt of a compound of Formula (II).

In some embodiments, R³ is bromo.

In some embodiments, the process forms a hydrochloride salt of a compound of Formula (II).

In some embodiments, R³ is chloro.

In some embodiments, the compound of Formula (V) is the R enantiomer.

In some embodiments, the compound of Formula (V) is the S enantiomer.

In some embodiments, the compound of Formula (V) is selected from: the R enantiomer, the S enantiomer or a mixture thereof.

In some embodiments, the reacting a compound of Formula (IV) with a compound of Formula (V) or a salt thereof is carried out in an alkylating solvent.

In some embodiments, the reacting a compound of Formula (IV) with a compound of Formula (V) or a salt thereof is carried out in a $C_1$-$C_3$ alcohol.

In some embodiments, the reacting a compound of Formula (IV) with a compound of Formula (V) or a salt thereof is carried out in ethanol.

In some embodiments, the reacting a compound of Formula (IV) with a compound of Formula (V) or a salt thereof is carried out in isopropanol.

In some embodiments, the reacting a compound of Formula (IV) with a compound of Formula (V) or a salt thereof is carried out at a temperature of about −20° C. to about 80° C.

In some embodiments, the reacting a compound of Formula (IV) with a compound of Formula (V) or a salt thereof is carried out at a temperature of about 0° C. to about 60° C.

In some embodiments, the reacting a compound of Formula (IV) with a compound of Formula (V) or a salt thereof is carried out at a temperature of about 20° C. to about 50° C.

In some embodiments, the molar ratio of the compound of Formula (IV) to the compound of Formula (V) is about 2:1 to about 1:2.

In some embodiments, the molar ratio of the compound of Formula (IV) to the compound of Formula (V) is about 1:1 to about 1:1.2.

Carboxylic Acid Activation Step

One aspect of the present invention pertains to processes for preparing compounds of Formula (III) or a salt thereof, comprising reacting a compound of Formula (VI):

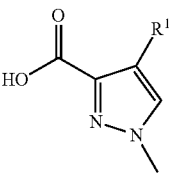

(VI)

or a salt thereof, with a compound of Formula (VII):

$$\underset{R^2}{\overset{O}{\underset{\|}{C}}}R^2 \qquad (VII)$$

or a salt thereof, to form a compound of Formula (III) or a salt thereof.

In some embodiments, $R^1$ is chloro.

In some embodiments, $R^1$ is bromo.

In some embodiments, $R^2$ is an N-linked heteroaryl.

In some embodiments, $R^2$ is 1H-imidazol-1-yl.

In some embodiments, $R^1$ is chloro and $R^2$ is 1H-imidazol-1-yl.

In some embodiments, the reacting a compound of Formula (VI) or a salt thereof with a compound of Formula (VII) or a salt thereof is carried out in a carboxylic acid activating solvent.

In some embodiments, the reacting a compound of Formula (VI) or a salt thereof with a compound of Formula (VII) or a salt thereof is carried out in an aprotic solvent.

In some embodiments, the reacting a compound of Formula (VI) or a salt thereof with a compound of Formula (VII) or a salt thereof is carried out in acetonitrile.

In some embodiments, the said reacting a compound of Formula (VI) or a salt thereof with a compound of Formula (VII) or a salt thereof is carried out at a temperature of about 20° C. to about reflux temperature.

In some embodiments, the reacting a compound of Formula (VI) or a salt thereof with a compound of Formula (VII) or a salt thereof is carried out at a temperature of about 40° C. to about 70° C.

In some embodiments, the reacting a compound of Formula (VI) or a salt thereof with a compound of Formula (VII) or a salt thereof is carried out at a temperature of about 50° C. to about 60° C.

In some embodiments, the molar ratio of the compound of Formula (VI) to the compound of Formula (VII) is about 2:1 to about 1:2.

In some embodiments, the molar ratio of the compound of Formula (VI) to the compound of Formula (VII) is about 1:1.

In Situ Carboxylic Acid Activation/Amide-Forming Step

One aspect of the present invention pertains to processes for preparing compounds of Formula (I) or a salt thereof, comprising the steps:

(a) reacting a compound of Formula (VI) or a salt thereof, with a compound of Formula (VII) or a salt thereof, wherein to form a compound of Formula (III) or a salt thereof; and (b) further reacting the compound of Formula (III) or a salt thereof in situ with a compound of Formula (II) or a salt thereof, to form a compound of Formula (I) or a salt thereof.

In some embodiments, the compound of Formula (I) is the R enantiomer.

In some embodiments, the compound of Formula (I) is the S enantiomer.

In some embodiments, $R^1$ is chloro.

In some embodiments, $R^1$ is bromo.

In some embodiments, $R^2$ is an N-linked heteroaryl.

In some embodiments, $R^2$ is 1H-imidazol-1-yl.

In some embodiments, step (a) is carried out in a carboxylic acid activating solvent.

In some embodiments, step (a) is carried out in an aprotic solvent.

In some embodiments, step (a) is carried out in acetonitrile.

In some embodiments, step (a) is carried out at a temperature of about 20° C. to about reflux temperature.

In some embodiments, step (a) is carried out at a temperature of about 40° C. to about 70° C.

In some embodiments, step (a) is carried out at a temperature of about 50° C. to about 60° C.

In some embodiments, the molar ratio of the compound of Formula (VI) to the compound of Formula (VII) is about 2:1 to about 1:2.

In some embodiments, the molar ratio of the compound of Formula (VI) to the compound of Formula (VII) is about 1:1.

In some embodiments, the process comprises reacting the compound of Formula (III) or a salt thereof in situ with a hydrobromide salt of a compound of Formula (II) to form a compound of Formula (I) or a salt thereof.

In some embodiments, the process comprises reacting said compound of Formula (III) or a salt thereof in situ with a hydrochloride salt of a compound of Formula (II) to form a compound of Formula (I) or a salt thereof.

In some embodiments, step (b) is carried out in the presence of a base.

In some embodiments, step (b) is carried out in the presence of a tertiary amine.

In some embodiments, step (b) is carried out in the presence of triethylamine.

In some embodiments, step (b) is carried out in the presence of a catalyst.

In some embodiments, step (b) is carried out in the presence of 2-hydroxypyridine.

In some embodiments, step (b) is carried out in the presence of N,N-dimethylaminopyridine.

In some embodiments, step (b) is carried out at a temperature of about 20° C. to about reflux temperature.

In some embodiments, step (b) is carried out at a temperature of about 40° C. to about reflux temperature.

In some embodiments, step (b) is carried out at a temperature of about 60° C. to about 80° C.

In some embodiments, step (b) is carried out in an amide-forming solvent.

In some embodiments, step (b) is carried out in an aprotic solvent.

In some embodiments, (b) is carried out in acetonitrile.

In some embodiments, the molar ratio of the compound of Formula (II) to the compound of Formula (III) is about 2:1 to about 0.5:1.

In some embodiments, the molar ratio of said compound of Formula (II) to said compound of Formula (III) is about 1:1.

Salt Formation

One aspect of the present invention pertains to processes for preparing salts of compounds of Formula (I):

(I)

comprising reacting a compound of Formula (I) with a salt-forming acid to form a salt of a compound of Formula (I) provided that the salt-forming acid is not trifluoroacetic acid.

In some embodiments, the compound of Formula (I) is the R enantiomer.

In some embodiments, the compound of Formula (I) is the S enantiomer.

In some embodiments, the compound of Formula (I) is selected from: the R enantiomer, the S enantiomer or a mixture thereof.

In some embodiments, the salt of a compound of Formula (I) is the hydrochloride salt.

In some embodiments, $R^1$ is chloro.

In some embodiments, $R^1$ is bromo.

In some embodiments, the reacting a compound of Formula (I) with a salt-forming acid is carried out in a salt-forming solvent.

In some embodiments, the reacting a compound of Formula (I) with a salt-forming acid is carried out in a salt-forming alcohol.

In some embodiments, the reacting a compound of Formula (I) with a salt-forming acid is carried out in isopropanol.

In some embodiments, the reacting a compound of Formula (I) with a salt-forming acid is carried out in ethanol.

In some embodiments, the reacting a compound of Formula (I) with a salt-forming acid is carried out at a temperature of about −10° C. to about reflux temperature.

In some embodiments, the reacting a compound of Formula (I) with a salt-forming acid is carried out at a temperature of about 10° C. to about 70° C.

In some embodiments, the reacting a compound of Formula (I) with a salt-forming acid is carried out at a temperature of about 20° C. to about 60° C.

In some embodiments, the reacting a compound of Formula (I) with a salt-forming acid is carried out at a temperature of about 30° C. to about 50° C.

In some embodiments, the salt-forming acid is hydrochloric acid.

The processes described herein can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), or mass spectrometry, or by chromatography such as high performance liquid chromatography (HPLC) or thin layer chromatography.

In some embodiments, preparation of compounds can involve the protection and deprotection of various chemical groups. The need for protection and deprotection, and the selection of appropriate protecting groups can be readily determined by one skilled in the art. The chemistry of protecting groups can be found, for example, in Greene and Wuts, *Protective Groups in Organic Synthesis*, $3^{rd}$ Ed., Wiley & Sons, 1999, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. In some embodiments, reactions can be carried out in the absence of solvent, such as when at least one of the reagents is a liquid or gas.

Suitable solvents can include halogenated solvents such as carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, hexafluorobenzene, 1,2,4-trichlorobenzene, o-dichlorobenzene, chlorobenzene, fluorobenzene, fluorotrichloromethane, chlorotrifluoromethane, bromotrifluoromethane, carbon tetrafluoride, dichlorofluoromethane, chlorodifluoromethane, trifluoromethane, 1,2-dichlorotetrafluorethane and hexafluoroethane.

Suitable ether solvents include: dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, or t-butyl methyl ether.

Suitable protic solvents can include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol.

Suitable aprotic solvents can include, by way of example and without limitation, tetrahydrofuran, N,N-dimethylformamide, N,N-dimethylacetamide, 1,3-dimethyl-3,4,5,6-tetrahydro-2(1H)-pyrimidinone, 1,3-dimethyl-2-imidazolidinone, N-methylpyrrolidinone, formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

Suitable hydrocarbon solvents include benzene, cyclohexane, pentane, hexane, toluene, cycloheptane, methylcyclohexane, heptane, ethylbenzene, o, m-, or p-xylene, octane, indane, nonane, or naphthalene.

Supercritical carbon dioxide can also be used as a solvent.

The reactions of the processes described herein can be carried out at appropriate temperatures which can be readily determined by one skilled in the art. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures).

The reactions of the processes described herein can be carried out in air or under an inert atmosphere. Typically, reactions containing reagents or products that are substantially reactive with air can be carried out using air-sensitive synthetic techniques that are well known to one skilled in the art.

In some embodiments, preparation of compounds can involve the addition of acids or bases to effect, for example, catalysis of a desired reaction or formation of salt forms such as acid addition salts.

Example acids can be inorganic or organic acids. Inorganic acids include hydrochloric acid, hydrobromic acid, sulfuric acid, phosphoric acid, and nitric acid. Organic acids include formic acid, acetic acid, propionic acid, butanoic acid, methanesulfonic acid, p-toluene sulfonic acid, benzenesulfonic acid, propiolic acid, butyric acid, 2-butynoic acid, vinyl acetic acid, pentanoic acid, hexanoic acid, heptanoic acid, octanoic acid, nonanoic acid and decanoic acid.

Example bases include lithium hydroxide, sodium hydroxide, potassium hydroxide, lithium carbonate, sodium carbonate, and potassium carbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include sodium and potassium salts of methyl, ethyl, n-propyl, i-propyl, n-butyl, t-butyl, trimethylsilyl and cyclohexyl substituted amides.

The compounds described herein can be asymmetric (e.g., having one or more stereocenters). All stereoisomers, such as enantiomers and diastereomers, are intended unless otherwise indicated. Salts of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis.

The processes described herein can be stereoselective such that any given reaction starting with one or more chiral reagents enriched in one stereoisomer forms a product that is also enriched in one stereoisomer. The reaction can be conducted such that the product of the reaction substantially retains one or more chiral centers present in the starting materials. The reaction can also be conducted such that the product of the reaction contains a chiral center that is substantially inverted relative to a corresponding chiral center present in the starting materials.

Resolution of racemic mixtures of compounds can be carried out by any of numerous methods known in the art. An example method includes fractional recrystallization (for example, diastereomeric salt resolution) using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of β-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention and salts thereof can also include all isotopes of atoms occurring in the intermediates or final salts. Isotopes include those atoms having the same atomic number but different mass numbers. For example, isotopes of hydrogen include tritium and deuterium.

Compounds of the invention and salts thereof can also include tautomeric forms, such as keto-enol tautomers. Tautomeric forms can be in equilibrium or sterically locked into one form by appropriate substitution.

Upon carrying out preparation of compounds according to the processes described herein, the usual isolation and purification operations such as concentration, filtration, extraction, solid-phase extraction, recrystallization, chromatography, and the like may be used, to isolate the desired products.

Pharmaceutically Acceptable Salts

One aspect of the present invention pertains to pharmaceutically acceptable salts of compounds of Formula (I):

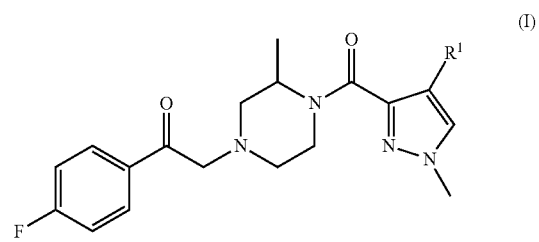

provided that the pharmaceutically acceptable salt is not a trifluoroacetate salt.

One aspect of the present invention pertains to hydrochloride salts of compounds of Formula (I).

In some embodiments, the compound of Formula (I) is the R enantiomer.

In some embodiments, the compound of Formula (I) is the S enantiomer.

In some embodiments, the compound of Formula (I) is selected from: the R enantiomer, the S enantiomer or a mixture thereof.

In some embodiments, $R^1$ is bromo.

In some embodiments, $R^1$ is chloro.

In some embodiments, the hydrochloride salt has a purity of 80% or greater.

In some embodiments, the hydrochloride salt has a purity of 90% or greater.

In some embodiments, the hydrochloride salt has a purity of 95% or greater.

In some embodiments, the hydrochloride salt has a purity of 99% or greater.

In some embodiments, the hydrochloride salt has a purity of 99.5% or greater.

In some embodiments, the hydrochloride salt comprises a hydrochloride salt of a compound of Formula (I) and the compound of Formula (I) in a ratio of about 4:1 or greater.

In some embodiments, the hydrochloride salt comprises a hydrochloride salt of a compound of Formula (I) and the compound of Formula (I) in a ratio of about 9:1 or greater.

In some embodiments, the hydrochloride salt comprises a hydrochloride salt of a compound of Formula (I) and the compound of Formula (I) in a ratio of about 19:1 or greater.

In some embodiments, the hydrochloride salt comprises a hydrochloride salt of a compound of Formula (I) and the compound of Formula (I) in a ratio of about 99:1 or greater.

Intermediates

One aspect of the present invention pertains to intermediates that are useful in the preparation of compounds of Formula (I) and salts thereof.

Some embodiments pertain to hydrobromide salts of a compound of Formula (II):

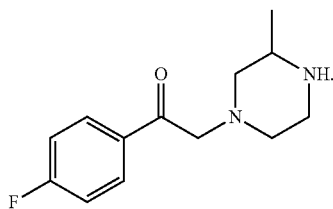
(II)

In some embodiments, the compound of Formula (II) is the R enantiomer.

In some embodiments, the compound of Formula (II) is the S enantiomer.

In some embodiments, the compound of Formula (II) is selected from: the R enantiomer, the S enantiomer or a mixture thereof.

In some embodiments, the hydrobromide salt has a purity of 80% or greater.

In some embodiments, the hydrobromide salt has a purity of 90% or greater.

In some embodiments, the hydrobromide salt has a purity of 95% or greater.

In some embodiments, the hydrobromide salt has a purity of 99% or greater.

In some embodiments, the hydrobromide salt has a purity of 99.5% or greater.

Some aspects of the present invention pertain to compositions comprising a hydrobromide salt of a compound of Formula (II).

In some embodiments, the composition comprising a hydrobromide salt of a compound of Formula (II) has a purity of 10% or greater.

In some embodiments, the composition comprising a hydrobromide salt of a compound of Formula (II) has a purity of 25% or greater.

In some embodiments, the composition comprising a hydrobromide salt of a compound of Formula (II) has a purity of 50% or greater.

In some embodiments, the composition comprising a hydrobromide salt of a compound of Formula (II) has a purity of 75% or greater.

In some embodiments, the composition comprising a hydrobromide salt of a compound of Formula (II) has a purity of 90% or greater.

In some embodiments, the composition comprising a hydrobromide salt of a compound of Formula (II) has a purity of 95% or greater.

In some embodiments, the composition comprising a hydrobromide salt of a compound of Formula (II) has a purity of 99% or greater.

In some embodiments, the composition comprising a hydrobromide salt of a compound of Formula (II) has a purity of 99.5% or greater.

Some embodiments pertain to compounds of Formula (III):

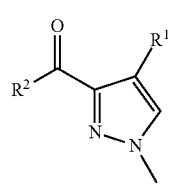
(III)

or a salt thereof, wherein:
$R^1$ is halogen; and
$R^2$ is 1H-imidazol-1-yl.

In some embodiments, $R^1$ is chloro.

In some embodiments, $R^1$ is bromo.

In some embodiments, the compound of Formula (III) has a purity of 80% or greater.

In some embodiments, the compound of Formula (III) has a purity of 90% or greater.

In some embodiments, the compound of Formula (III) has a purity of 95% or greater.

In some embodiments, the compound of Formula (III) has a purity of 99% or greater.

In some embodiments, the compound of Formula (III) has a purity of 99.5% or greater.

Some aspects of the present invention pertain to compositions comprising a compound of Formula (III).

In some embodiments, the composition comprising a compound of Formula (III) has a purity of 1% or greater.

In some embodiments, the composition comprising a compound of Formula (III) has a purity of 10% or greater.

In some embodiments, the composition comprising a compound of Formula (III) has a purity of 25% or greater.

In some embodiments, the composition comprising a compound of Formula (III) has a purity of 50% or greater.

In some embodiments, the composition comprising a compound of Formula (III) has a purity of 75% or greater.

In some embodiments, the composition comprising a compound of Formula (III) has a purity of 90% or greater.

In some embodiments, the composition comprising a compound of Formula (III) has a purity of 95% or greater.

In some embodiments, the composition comprising a compound of Formula (III) has a purity of 99% or greater.

In some embodiments, the composition comprising a compound of Formula (III) has a purity of 99.5% or greater.

Indications and Methods of Treatment

In addition to the foregoing beneficial uses for the modulators of $5\text{-HT}_{2A}$ serotonin receptor activity disclosed herein, the salts disclosed herein are believed to be useful in the treatment of several additional diseases and disorders, and in the amelioration of symptoms thereof. Without limitation, these include the following:

1. Sleep Disorders

It is reported in the National Sleep Foundation's 2002 Sleep In America Poll, more than one-half of the adults surveyed (58%) report having experienced one or more symptoms of insomnia at least a few nights a week in the past year. Additionally, about three in ten (35%) say they have experienced insomnia-like symptoms every night or almost every night.

The normal sleep cycle and sleep architecture can be disrupted by a variety of organic causes as well as environmental influences. According to the International Classification of Sleep Disorders, there are over 80 recognized sleep disorders. Of these, salts of the present invention are effective, for example, in any one or more of the following sleep disorders (ICSD—International Classification of Sleep Disorders: Diagnostic and Coding Manual. *Diagnostic Classification Steering Committee*; American Sleep Disorders Association, 1990):

A. Dyssomnias
 a. Intrinsic Sleep Disorders:
Psychophysiological insomnia, sleep state misperception, idiopathic insomnia, obstructive sleep apnea syndrome, central sleep apnea syndrome, central alveolar hypoventilation syndrome, periodic limb movement disorder, restless leg syndrome and intrinsic sleep disorder NOS (not otherwise specified).

b. Extrinsic Sleep Disorders:

Inadequate sleep hygiene, environmental sleep disorder, altitude insomnia, adjustment sleep disorder, insufficient sleep syndrome, limit-setting sleep disorder, sleep onset association disorder, nocturnal eating (drinking) syndrome, hypnotic-dependent sleep disorder, stimulant-dependent sleep disorder, alcohol-dependent sleep disorder, toxin-induced sleep disorder and extrinsic sleep disorder NOS.

c. Circadian Rhythm Sleep Disorders:

Time zone change (jet lag) syndrome, shift work sleep disorder, irregular sleep-wake pattern, delayed sleep phase syndrome, advanced sleep phase syndrome, non-24-hour sleep-wake disorder and circadian rhythm sleep disorder NOS.

B. Parasomnias a. Arousal Disorders:

Confusional arousals, sleepwalking and sleep terrors.

b. Sleep-Wake Transition Disorders:

Rhythmic movement disorder, sleep starts, sleep talking and nocturnal leg cramps.

C. Sleep Disorders Associated with Medical/Psychiatric Disorders a. Associated with Mental Disorders:

Psychoses, mood disorders, anxiety disorders, panic disorders and alcoholism.

b. Associated with Neurological Disorders:

Cerebral degenerative disorders, dementia, Parkinsonism, fatal familial insomnia, sleep-related epilepsy, electrical status epilepticus of sleep and sleep-related headaches.

c. Associated with Other Medical Disorders:

Sleeping sickness, nocturnal cardiac ischemia, chronic obstructive pulmonary disease, sleep-related asthma, sleep-related gastroesophageal reflux, peptic ulcer disease, fibrositis syndrome, osteoarthritis, rheumatoid arthritis, fibromyalgia and post-surgical.

The effects of sleep deprivation are more than excessive daytime sleepiness. Chronic insomniacs report elevated levels of stress, anxiety, depression and medical illnesses (National Institutes of Health, National Heart, Lung, and Blood Institute, *Insomnia Facts Sheet*, October 1995). Preliminary evidence suggests that having a sleep disorder that causes significant loss of sleep may contribute to increased susceptibility to infections due to immunosuppression, cardiovascular complications such as hypertension, cardiac arrhythmias, stroke, and myocardial infarction, compromised glucose tolerance, increased obesity and metabolic syndrome. Salts of the present invention are useful to prevent or alleviate these complications by improving sleep quality.

The most common class of medications for the majority of sleep disorders are the benzodiazepines, but the adverse effect profile of benzodiazepines include daytime sedation, diminished motor coordination, and cognitive impairments. Furthermore, the National Institutes of Health Consensus conference on Sleeping Pills and Insomnia in 1984 have developed guidelines discouraging the use of such sedative-hypnotics beyond 4-6 weeks because of concerns raised over drug misuse, dependency, withdrawal and rebound insomnia. Therefore, it is desirable to have a pharmacological agent for the treatment of insomnia, which is more effective and/or has fewer side effects than those currently used. In addition, benzodiazepines are used to induce sleep, but have little to no effect on the maintenance of sleep, sleep consolidation or slow wave sleep. Therefore, sleep maintenance disorders are not currently well treated.

Clinical studies with agents of a similar mechanism of action as are salts of the present invention have demonstrated significant improvements on objective and subjective sleep parameters in normal, healthy volunteers as well as patients with sleep disorders and mood disorders [Sharpley A. L., et al. Slow Wave Sleep in Humans: Role of 5-HT$_{2A}$ and 5HT$_{2c}$ Receptors. *Neuropharmacology*, 1994, Vol. 33(3/4):467-71; Winokur A., et al. Acute Effects of Mirtazapine on Sleep Continuity and Sleep Architecture in Depressed Patients: A Pilot Study. *Soc. of Biol. Psych.*, 2000, Vol. 48:75-78; and Landolt H. P., et al. Serotonin-2 Receptors and Human Sleep: Effect of Selective Antagonist on EEG Power Spectra. *Neuropsychopharmacology*, 1999, Vol. 21(3):455-66].

Some sleep disorders are sometimes found in conjunction with other conditions and accordingly those conditions are treatable by salts of compounds of Formula (I). For example, but not limited to, patients suffering from mood disorders typically suffer from a sleep disorder that can be treatable by salts of compounds of Formula (I). Having one pharmacological agent which treats two or more existing or potential conditions, as does the present invention, is more cost effective, leads to better compliance and has fewer side effects than taking two or more agents.

It is an object of the present invention to provide a therapeutic agent for the use in treating sleep disorders. It is another object of the present invention to provide one pharmaceutical agent, which may be useful in treating two or more conditions wherein one of the conditions is a sleep disorder. Salts of the present invention described herein may be used alone or in combination with a mild sleep inducer (i.e. antihistamine).

Sleep Architecture

Sleep comprises two physiological states: Non rapid eye movement (NREM) and rapid eye movement (REM) sleep. NREM sleep consists of four stages, each of which is characterized by progressively slower brain wave patterns, with the slower patterns indicating deeper sleep. So called delta sleep, stages 3 and 4 of NREM sleep, is the deepest and most refreshing type of sleep. Many patients with sleep disorders are unable to adequately achieve the restorative sleep of stages 3 and 4. In clinical terms, patients' sleep patterns are described as fragmented, meaning the patient spends a lot of time alternating between stages 1 and 2 (semi-wakefulness) and being awake and very little time in deep sleep. As used herein, the term "fragmented sleep architecture" means an individual, such as a sleep disorder patient, spends the majority of their sleep time in NREM sleep stages 1 and 2, lighter periods of sleep from which the individual can be easily aroused to a waking state by limited external stimuli. As a result, the individual cycles through frequent bouts of light sleep interrupted by frequent awakenings throughout the sleep period. Many sleep disorders are characterized by a fragmented sleep architecture. For example, many elderly patients with sleep complaints have difficulty achieving long bouts of deep, refreshing sleep (NREM stages 3 and 4) and instead spend the majority of their sleep time in NREM sleep stages 1 and 2.

In contrast to fragmented sleep architecture, as used herein the term "sleep consolidation" means a state in which the number of NREM sleep bouts, particularly Stages 3 and 4, and the length of those sleep bouts are increased, while the number and length of waking bouts are decreased. In essence, the architecture of the sleep disorder patient is consolidated to a sleeping state with increased periods of sleep and fewer awakenings during the night and more time is spent in slow wave sleep (stages 3 and 4) with fewer oscillation stage 1 and 2 sleep. Salts of the present invention can be effective in consolidating sleep patterns so that the patient with previously fragmented sleep can now achieve restorative, delta-wave sleep for longer, more consistent periods of time.

As sleep moves from stage 1 into later stages, heart rate and blood pressure drop, metabolic rate and glucose consumption fall, and muscles relax. In normal sleep architecture, NREM sleep makes up about 75% of total sleep time; stage 1 accounting for 5-10% of total sleep time, stage 2 for about 45-50%, stage 3 approximately 12%, and stage 4 13-15%. About 90 minutes after sleep onset, NREM sleep gives way to the first REM sleep episode of the night. REM makes up approximately 25% of total sleep time. In contrast to NREM sleep, REM sleep is characterized by high pulse, respiration, and blood pressure, as well as other physiological patterns similar to those seen in the active waking stage. Hence, REM sleep is also known as "paradoxical sleep." Sleep onset occurs during NREM sleep and takes 10-20 minutes in healthy young adults. The four stages of NREM sleep together with a REM phase form one complete sleep cycle that is repeated throughout the duration of sleep, usually four or five times. The cyclical nature of sleep is regular and reliable: a REM period occurs about every 90 minutes during the night. However, the first REM period tends to be the shortest, often lasting less than 10 minutes, whereas the later REM periods may last up to 40 minutes. With aging, the time between retiring and sleep onset increases and the total amount of night-time sleep decreases because of changes in sleep architecture that impair sleep maintenance as well as sleep quality. Both NREM (particularly stages 3 and 4) and REM sleep are reduced. However, stage 1 NREM sleep, which is the lightest sleep, increases with age.

As used herein, the term "delta power" means a measure of the duration of EEG activity in the 0.5 to 3.5 Hz range during NREM sleep and is thought to be a measure of deeper, more refreshing sleep. Delta power is hypothesized to be a measure of a theoretical process called Process S and is thought to be inversely related to the amount of sleep an individual experiences during a given sleep period. Sleep is controlled by homeostatic mechanisms; therefore, the less one sleeps the greater the drive to sleep. It is believed that Process S builds throughout the wake period and is discharged most efficiently during delta power sleep. Delta power is a measure of the magnitude of Process S prior to the sleep period. The longer one stays awake, the greater Process S or drive to sleep and thus the greater the delta power during NREM sleep. However, individuals with sleep disorders have difficulty achieving and maintaining delta wave sleep, and thus have a large build-up of Process S with limited ability to discharge this buildup during sleep. $5\text{-HT}_{2A}$ agonists tested preclinically and clinically mimic the effect of sleep deprivation on delta power, suggesting that subjects with sleep disorders treated with a $5\text{-HT}_{2A}$ inverse agonist or antagonist will be able to achieve deeper sleep that is more refreshing. These same effects have not been observed with currently marketed pharmacotherapies. In addition, currently marketed pharmacotherapies for sleep have side effects such as hangover effects or addiction that are associated with the GABA receptor. $5\text{-HT}_{2A}$ inverse agonists do not target the GABA receptor and so these side effects are not a concern.

Subjective and Objective Determinations of Sleep Disorders:

There are a number of ways to determine whether the onset, duration or quality of sleep (e.g. non-restorative or restorative sleep) is impaired or improved. One method is a subjective determination of the patient, e.g., do they feel drowsy or rested upon waking. Other methods involve the observation of the patient by another during sleep, e.g., how long it takes the patient to fall asleep, how many times the patient wakes up during the night, how restless is the patient during sleep, etc. Another method is to measure the stages of sleep objectively using polysomnography.

Polysomnography is the monitoring of multiple electrophysiological parameters during sleep and generally includes measurement of EEG activity, electroculographic activity and electromyographic activity, as well as other measurements. These results, along with observations, can measure not only sleep latency (the amount of time required to fall asleep), but also sleep continuity (overall balance of sleep and wakefulness) and sleep consolidation (percent of sleeping time spent in delta-wave or restorative sleep) which may be an indication of the quality of sleep.

There are five distinct sleep stages, which can be measured by polysomnography: rapid eye movement (REM) sleep and four stages of non-rapid eye movement (NREM) sleep (stages 1, 2, 3 and 4). Stage 1 NREM sleep is a transition from wakefulness to sleep and occupies about 5% of time spent asleep in healthy adults. Stage 2 NREM sleep, which is characterized by specific EEG waveforms (sleep spindles and K complexes), occupies about 50% of time spent asleep. Stages 3 and 4 NREM sleep (also known collectively as slow-wave sleep and delta-wave sleep) are the deepest levels of sleep and occupy about 10-20% of sleep time. REM sleep, during which the majority of vivid dreams occur, occupies about 20-25% of total sleep.

These sleep stages have a characteristic temporal organization across the night. NREM stages 3 and 4 tend to occur in the first one-third to one-half of the night and increase in duration in response to sleep deprivation. REM sleep occurs cyclically through the night. Alternating with NREM sleep about every 80-100 minutes. REM sleep periods increase in duration toward the morning. Human sleep also varies characteristically across the life span. After relative stability with large amounts of slow-wave sleep in childhood and early adolescence, sleep continuity and depth deteriorate across the adult age range. This deterioration is reflected by increased wakefulness and stage 1 sleep and decreased stages 3 and 4 sleep.

In addition, the salts of the invention can be useful for the treatment of the sleep disorders characterized by excessive daytime sleepiness such as narcolepsy. Inverse agonists at the serotonin $5\text{-HT}_{2A}$ receptor improve the quality of sleep at nighttime which can decrease excessive daytime sleepiness.

Accordingly, another aspect of the present invention relates to the therapeutic use of salts of the present invention for the treatment of sleep disorders. Salts of the present invention are potent inverse agonists at the serotonin $5\text{-HT}_{2A}$ receptor and can be effective in the treatment of sleep disorders by promoting one or more of the following: reducing the sleep onset latency period (measure of sleep induction), reducing the number of nighttime awakenings, and prolonging the amount of time in delta-wave sleep (measure of sleep quality enhancement and sleep consolidation) without effecting REM sleep. In addition, salts of the present invention can be effective either as a monotherapy or in combination with sleep inducing agents, for example but not limited to, antihistamines.

Pharmacodynamic Effects of the Selective 5-HT$_{2A}$ Inverse Agonist APD125 in Healthy Adults APD125, a potent and selective 5-HT$_{2A}$ serotonin receptor inverse agonist is a member of the genus disclosed in the European Patent EP1558582. In Phase 1 trials, APD125 showed vigilance-lowering effects on waking EEG, with maximal effects at 40-80 mg; peak effects were observed at 2-4 h after dosing. In the afternoon nap model of insomnia in normal volunteers, APD125 increased slow wave sleep and associated parameters in a dose-dependent manner, primarily during the early part of sleep. These effects occurred at the expense of REM sleep. Sleep onset latency was not decreased by APD125. In the afternoon nap model, APD125 decreased microarousals, the number of sleep stage shifts, and number of awakenings after sleep onset.

In a Phase 2 trial, when compared to placebo, patients treated with APD 125 experienced statistically significant improvements in measurements of sleep maintenance, or the ability to maintain sleep during the night after falling asleep. The improvements in measurements of sleep maintenance were achieved without any limiting next day cognitive effects. The data from the APD 125 Phase 2 study are consistent with Phase 1 data and support further development of APD125 for the treatment of insomnia patients who have difficulty maintaining sleep.

In conclusion, APD125, a 5-HT$_{2A}$ serotonin receptor inverse agonist, improved parameters of sleep consolidation and maintenance in humans. Thus, salts of the present invention, also highly selective 5-HT$_{2A}$ serotonin receptor inverse agonists, will offer similar improvements in sleep parameters.

2. Antiplatelet Therapies (Conditions Related to Platelet Aggregation)

Antiplatelet agents (antiplatelets) are prescribed for a variety of conditions. For example, in coronary artery disease they are used to help prevent myocardial infarction or stroke in patients who are at risk of developing obstructive blood clots (e.g., coronary thrombosis).

In a myocardial infarction (heart attack), the heart muscle does not receive enough oxygen-rich blood because of a blockage in the coronary blood vessels. If taken while an attack is in progress or immediately afterward (preferably within 30 minutes), antiplatelets can reduce the damage to the heart.

A transient ischemic attack ("TIA" or "mini-stroke") is a brief interruption of oxygen flow to the brain due to decreased blood flow through arteries, usually due to an obstructing blood clot. Antiplatelet drugs have been found to be effective in preventing TIAs.

Angina is a temporary and often recurring chest pain, pressure or discomfort caused by inadequate oxygen-rich blood flow (ischemia) to some parts of the heart. In patients with angina, antiplatelet therapy can reduce the effects of angina and the risk of myocardial infarction.

Stroke is an event in which the brain does not receive enough oxygen-rich blood, usually due to blockage of a cerebral blood vessel by a blood clot. In high-risk patients, taking antiplatelets regularly has been found to prevent the formation of blood clots that cause first or second strokes.

Angioplasty is a catheter-based technique used to open arteries obstructed by a blood clot. Whether or not stenting is performed immediately after this procedure to keep the artery open, antiplatelets can reduce the risk of forming additional blood clots following the procedure(s).

Coronary bypass surgery is a surgical procedure in which an artery or vein is taken from elsewhere in the body and grafted to a blocked coronary artery, rerouting blood around the blockage and through the newly attached vessel. After the procedure, antiplatelets can reduce the risk of secondary blood clots.

Atrial fibrillation is the most common type of sustained irregular heart rhythm (arrhythmia). Atrial fibrillation affects about two million Americans every year. In atrial fibrillation, the atria (the heart's upper chambers) rapidly fire electrical signals that cause them to quiver rather than contract normally. The result is an abnormally fast and highly irregular heartbeat. When given after an episode of atrial fibrillation, antiplatelets can reduce the risk of blood clots forming in the heart and traveling to the brain (embolism).

5-HT$_{2A}$ serotonin receptors are expressed on smooth muscle of blood vessels and 5-HT secreted by activated platelets causes vasoconstriction as well as activation of additional platelets during clotting. There is evidence that a 5-HT$_{2A}$ inverse agonist will inhibit platelet aggregation and thus be a potential treatment as an antiplatelet therapy (see Satimura, K., et al., *Clin. Cardiol.* 2002 Jan. 25 (1):28-32; and Wilson, H. C. et al., *Thromb. Haemost.* 1991 Sep. 2; 66(3):355-60).

5-HT$_{2A}$ inverse agonists can be used to treat, for example, claudication or peripheral artery disease as well as cardio-vascular complications (see *Br. Med. J.* 298: 424-430, 1989), arterial thrombosis (see, Pawlak, D. et al. *Thrombosis Research* 90: 259-270, 1998), atherosclerosis (see, Hayashi, T. et al. Atherosclerosis 168: 23-31, 2003), vasoconstriction caused by serotonin (see, Fujiwara, T. and Chiba, S. *Journal of Cardiovascular Pharmacology* 26: 503-510, 1995), restenosis of arteries following angioplasty or stent placement (see, Fujita, M. et al. *Am. Heart J.* 145:e16, 2003). It can also be used alone or in combination with thrombolytic therapy, for example, tissue plasminogen activator (tPA) (see, Yamashita, T. et al. *Haemostasis* 30:321-332, 2000), to provide cardioprotection following MI or postischemic myocardial dysfunction (see, Muto, T. et al. *Mol. Cell. Biochem.* 272: 119-132, 2005) or protection from ischemic injury during percutaneous coronary intervention (see, Horibe, E. *Circulation Research* 68: 68-72, 2004), and the like, including complications resulting therefrom.

5-HT$_{2A}$ inverse antagonists can increase circulating adiponectin in patients, suggesting that they would also be useful in protecting patients against indications that are linked to adiponectin, for example, myocardial ischemia reperfusion injury and atherosclerosis (see Nomura et al. *Blood Coagulation and Fibrinolysis* 2005, 16, 423-428).

The 5-HT$_{2A}$ inverse agonists disclosed herein provide beneficial improvement in microcirculation to patients in need of antiplatelet therapy by antagonizing the vasoconstrictive products of the aggregating platelets in, for example and not limited to the indications described above. Accordingly, in some embodiments, the present invention provides methods for reducing platelet aggregation in a patient in need thereof comprising administering to the patient a composition comprising a 5-HT$_{2A}$ inverse agonist disclosed herein. In further embodiments, the present invention provides methods for treating coronary artery disease, myocardial infarction, transient ischemic attack, angina, stroke, atrial fibrillation, or a symptom of any of the foregoing in a patient in need of the treatment, comprising administering to the patient a composition comprising a 5-HT$_{2A}$ inverse agonist disclosed herein.

In further embodiments, the present invention provides methods for reducing risk of blood clot formation in an angioplasty or coronary bypass surgery patient, or a patient suffering from atrial fibrillation, comprising administering to the patient a composition comprising a 5-HT$_{2A}$ inverse agonist disclosed herein at a time where such risk exists.

3. Asthma

5-HT (5-hydroxytryptamine) has been linked to the pathophysiology of acute asthma (see Cazzola, M. and Matera, M. G., *Trends Pharmacol. Sci.* 21: 201-202, 2000; and De Bie, J. J. et al., *British J. Pharm.*, 1998, 124, 857-864). The salts of the present invention disclosed herein are useful in the treatment of asthma, and the treatment of the symptoms thereof. Accordingly, in some embodiments, the present invention provides methods for treating asthma in a patient in need of the treatment, comprising administering to the patient a composition comprising a 5-HT$_{2A}$ inverse agonist disclosed herein. In further embodiments, methods are provided for treating a symptom of asthma in a patient in need of the treatment, comprising administering to the patient a composition comprising a 5-HT$_{2A}$ inverse agonist disclosed herein.

4. Agitation

Agitation is a well-recognized behavioral syndrome with a range of symptoms, including hostility, extreme excitement, poor impulse control, tension and uncooperativeness (See Cohen-Mansfield J., and Billig, N., (1986), Agitated Behaviors in the Elderly. I. A Conceptual Review. *J. Am. Geriatr. Soc.* 34(10): 711-721).

Agitation is a common occurrence in the elderly and is often associated with dementia such as those caused by Alzheimer's disease, Lewy Body, Parkinson's, and Huntington's, which are degenerative diseases of the nervous system. Diseases that affect blood vessels, such as stroke, or multi-infarct dementia, which is caused by multiple strokes in the brain can also induce agitation. Alzheimer's disease accounts for approximately 50 to 70% of all dementias (See Koss E., et al., (1997), Assessing patterns of agitation in Alzheimer's disease patients with the Cohen-Mansfield Agitation Inventory. The Alzheimer's Disease Cooperative Study. *Alzheimer Dis. Assoc. Disord.* 11(suppl 2): S45-S50).

An estimated 5% of people aged 65 and older and up to 20% of those aged 80 and older are affected by dementia; of these sufferers, nearly half exhibit behavioral disturbances, such as agitation, wandering and violent outbursts.

Agitated behaviors can also be manifested in cognitively intact elderly people and by those with psychiatric disorders other than dementia.

Agitation is often treated with antipsychotic medications such as haloperidol in nursing home and other assisted care settings. There is emerging evidence that agents acting at the 5-HT$_{2A}$ serotonin receptors in the brain have the effects of reducing agitation in patients, including Alzheimer's dementia (See Katz, I. R., et al., *J. Clin. Psychiatry* 1999 February, 60(2):107-115; and Street, J. S., et al., *Arch. Gen. Psychiatry* 2000 October, 57(10):968-976).

The salts of the invention disclosed herein are useful for treating agitation and symptoms thereof. Thus, in some embodiments, the present invention provides methods for treating agitation in a patient in need of such treatment comprising administering to the patient a composition comprising a 5-HT$_{2A}$ inverse agonist disclosed herein. In some embodiments, the agitation is due to a psychiatric disorder other than dementia. In some embodiments, the present invention provides methods for treatment of agitation or a symptom thereof in a patient suffering from dementia comprising administering to the patient a composition comprising a 5-HT$_{2A}$ inverse agonist disclosed herein. In some embodiments of such methods, the dementia is due to a degenerative disease of the nervous system, for example and without limitation, Alzheimer's disease, Lewy Body, Parkinson's disease, and Huntington's disease, or dementia due to diseases that affect blood vessels, including, without limitation, stroke and multi-infarct dementia. In some embodiments, methods are provided for treating agitation or a symptom thereof in a patient in need of such treatment, where the patient is a cognitively intact elderly patient, comprising administering to the patient a composition comprising a 5-HT$_{2A}$ inverse agonist disclosed herein.

5. Add-on Therapy to Haloperidol in the Treatment of Schizophrenia and Other Disorders Schizophrenia is a psychopathic disorder of unknown origin, which usually appears for the first time in early adulthood and is marked by a number of characteristics, psychotic symptoms, progression, phasic development and deterioration in social behavior and professional capability in the region below the highest level ever attained. Characteristic psychotic symptoms are disorders of thought content (multiple, fragmentary, incoherent, implausible or simply delusional contents or ideas of persecution) and of mentality (loss of association, flight of imagination, incoherence up to incomprehensibility), as well as disorders of perceptibility (hallucinations), of emotions (superficial or inadequate emotions), of self-perception, of intentions and impulses, of interhuman relationships, and finally psychomotoric disorders (such as catatonia). Other symptoms are also associated with this disorder: see, *American Statistical and Diagnostic Handbook*.

Haloperidol (Haldol) is a potent dopamine D$_2$ receptor antagonist. It is widely prescribed for acute schizophrenic symptoms, and is very effective for the positive symptoms of schizophrenia. However, Haldol is not effective for the negative symptoms of schizophrenia and may actually induce negative symptoms as well as cognitive dysfunction. In accordance with some methods of the invention, adding a 5-HT$_{2A}$ inverse agonist concomitantly with Haldol will provide benefits including the ability to use a lower dose of Haldol without losing its effects on positive symptoms, while reducing or eliminating its inductive effects on negative symptoms, and prolonging relapse to the patient's next schizophrenic event.

Haloperidol is used for treatment of a variety of behavioral disorders, drug induced psychosis, excitative psychosis, Gilles de la Tourette's syndrome, manic disorders, psychosis (organic and NOS), psychotic disorder, psychosis, schizophrenia (acute, chronic and NOS). Further uses include in the treatment of infantile autism, Huntington's chorea, and nausea and vomiting from chemotherapy and chemotherapeutic antibodies. Administration of 5-HT$_{2A}$ inverse agonists disclosed herein with haloperidol also will provide benefits in these indications.

In some embodiments, the present invention provides methods for treating a behavioral disorder, drug induced psychosis, excitative psychosis, Gilles de la Tourette's syndrome, manic disorders, psychosis (organic and NOS), psychotic disorder, psychosis, schizophrenia (acute, chronic and NOS) comprising administering to the patient a dopamine D$_2$ receptor antagonist and a 5-HT$_{2A}$ inverse agonist disclosed herein.

In some embodiments, the present invention provides methods for treating a behavioral disorder, drug induced psychosis, excitative psychosis, Gilles de la Tourette's syndrome, manic disorders, psychosis (organic and NOS), psychotic disorder, psychosis, schizophrenia (acute, chronic and NOS) comprising administering to the patient haloperidol and a 5-HT$_{2A}$ inverse agonist disclosed herein.

In some embodiments, the present invention provides methods for treating infantile autism, Huntington's chorea, or nausea and vomiting from chemotherapy or chemotherapeutic antibodies comprising administering to the patient a dopamine $D_2$ receptor antagonist and a 5-HT$_{2A}$ inverse agonist disclosed herein.

In some embodiments, the present invention provides methods for treating infantile autism, Huntington's chorea, or nausea and vomiting from chemotherapy or chemotherapeutic antibodies comprising administering to the patient haloperidol and a 5-HT$_{2A}$ inverse agonist disclosed herein.

In further embodiments, the present invention provides methods for treating schizophrenia in a patient in need of the treatment comprising administering to the patient a dopamine $D_2$ receptor antagonist and a 5-HT$_{2A}$ inverse agonist disclosed herein. Preferably, the dopamine $D_2$ receptor antagonist is haloperidol.

The administration of the dopamine $D_2$ receptor antagonist can be concomitant with administration of the 5-HT$_{2A}$ inverse agonist, or they can be administered at different times. Those of skill in the art will easily be able to determine appropriate dosing regimes for the most efficacious reduction or elimination of deleterious haloperidol effects. In some embodiments, haloperidol and the 5-HT$_{2A}$ inverse agonist are administered in a single dosage form, and in other embodiments, they are administered in separate dosage forms.

The present invention further provides methods of alleviating negative symptoms of schizophrenia induced by the administration of haloperidol to a patient suffering from schizophrenia, comprising administering to the patient a 5-HT$_{2A}$ inverse agonist as disclosed herein.

6. Diabetic-Related Pathologies

Although hyperglycemia is the major cause for the pathogenesis of diabetic complications such as diabetic peripheral neuropathy (DPN), diabetic nephropathy (DN) and diabetic retinopathy (DR), increased plasma serotonin concentration in diabetic patients has also been implicated to play a role in disease progression (Pietraszek, M. H., et al. *Thrombosis Res.* 1992, 66(6), 765-74; and Andrzejewska-Buczko J., et al., *Klin. Oczna.* 1996; 98(2), 101-4). Serotonin is believed to play a role in vasospasm and increased platelet aggregability. Improving microvascular blood flow is beneficial to diabetic complications.

A recent study by Cameron and Cotter in *Naunyn Schmiedebergs Arch. Pharmacol.* 2003 June; 367(6):607-14, used a 5-HT$_{2A}$ antagonist experimental drug AT-1015, and other non-specific 5-HT$_{2A}$ antagonists including ritanserin and sarpogrelate. These studies found that all three drugs were able to produce a marked correction (82.6-99.7%) of a 19.8% sciatic motor conduction deficit in diabetic rats. Similarly, 44.7% and 14.9% reductions in sciatic endoneurial blood flow and saphenous sensory conduction velocity were completely reversed.

In a separate patient study, sarpogrelate was evaluated for the prevention of the development or progression of diabetic nephropathy (Takahashi, T., et al., *Diabetes. Res. Clin. Pract.* 2002 November; 58(2):123-9). In the trial of 24 months of treatment, sarpogrelate significantly reduced urinary albumin excretion level.

7. Glaucoma

Topical ocular administration of 5-HT$_2$ receptor antagonists result in a decrease in intra ocular pressure (IOP) in monkeys (Chang et al., *J. Ocul. Pharmacol.* 1:137-147 (1985)) and humans (Mastropasqua et al., *Acta. Ophthalmol. Scand. Suppl.* 224:24-25 (1997)) indicating utility for similar compounds such as 5-HT$_{2A}$ inverse agonists in the treatment of ocular hypertension associated with glaucoma. The 5-HT$_2$ receptor antagonist ketanserin (Mastropasqua supra) and sarpogrelate (Takenaka et al., *Investig. Ophthalmol. Vis. Sci.* 36:S734 (1995)) have been shown to significantly lower IOP in glaucoma patients.

8. Progressive Multifocal Leukoencephalopathy

Progressive multifocal leukoencephalopathy (PML) is a lethal demyelinating disease caused by an opportunistic viral infection of oligodendrocytes in immunocompromised patients. The causative agent is JC virus, a ubiquitous papovavirus that infects the majority of the population before adulthood and establishes a latent infection in the kidney. In immunocompromised hosts, the virus can reactivate and productively infect oligodendrocytes. This previously rare condition, until 1984 reported primarily in persons with underlying lymphoproliferative disorders, is now more common because it occurs in 4% of patients with AIDS. Patients usually present with relentlessly progressive focal neurologic defects, such as hemiparesis or visual field deficits, or with alterations in mental status. On brain MRI, one or more white matter lesions are present; they are hyperintense on T2-weighted images and hypointense on T1-weighted images. There is no mass effect, and contrast enhancement is rare. Diagnosis can be confirmed by brain biopsy, with demonstration of virus by in situ hybridization or immunocytochemistry. Polymerase chain reaction amplification of JC virus sequences from the CSF can confirm diagnosis without the need for biopsy [Antinori et al., *Neurology* (1997) 48:687-694; Berger and Major, *Seminars in Neurology* (1999) 19:193-200; and Portegies, et al., *Eur. J. Neurol.* (2004) 11:297-304]. Currently, there is no effective therapy. Survival after diagnosis is about 3 to 5 months in AIDS patients.

JC virus enters cells by receptor-mediated clathrin-dependent endocytosis. Binding of JC virus to human glial cells (e.g., oligodendrocytes) induces an intracellular signal that is critical for entry and infection by a ligand-inducible clathrin-dependent mechanism [Querbes et al., *J. Virology* (2004) 78:250-256]. Recently, 5-HT$_{2A}$ was shown to be the receptor on human glial cells mediating infectious entry of JC virus by clathrin-dependent endocytosis [Elphick et al., *Science* (2004) 306:1380-1383]. 5-HT$_{2A}$ antagonists, including ketanserin and ritanserin, inhibited JC virus infection of human glial cells. Ketanserin and ritanserin have inverse agonist activity at 5-HT$_{2A}$.

5-HT$_{2A}$ antagonists including inverse agonists have been contemplated to be useful in the treatment of PML [Elphick et al., *Science* (2004) 306:1380-1383]. Prophylactic treatment of HIV-infected patients with 5-HT$_{2A}$ antagonists is envisioned to prevent the spread of JC virus to the central nervous system and the development of PML. Aggressive therapeutic treatment of patients with PML is envisioned to reduce viral spread within the central nervous system and prevent additional episodes of demyelination.

One aspect of the present invention encompasses methods for the treatment of progressive multifocal leukoencephalopathy in an individual comprising administering to the individual in need thereof a therapeutically effective amount of a salt according to any of the embodiments described herein or a pharmaceutical composition.

In some embodiments, the individual in need thereof has a lymphoproliferative disorder. In some embodiments, the lymphoproliferative disorder is leukemia or lymphoma. In some embodiments, the leukemia or lymphoma is chronic lymphocytic leukemia, Hodgkin's disease, or the like.

In some embodiments, the individual in need thereof has a myeloproliferative disorder.

In some embodiments, the individual in need thereof has carcinomatosis.

In some embodiments, the individual in need thereof has a granulomatous or inflammatory disease. In some embodiments, the granulomatous or inflammatory disease is tuberculosis or sarcoidosis.

In some embodiments, the individual in need thereof is immunocompromised. In some embodiments, the immunocompromised individual has impaired cellular immunity. In some embodiments, the impaired cellular immunity comprises impaired T-cell immunity.

In some embodiments, the individual in need thereof is infected with HIV. In some embodiments, the HIV-infected individual has a CD4+ cell count of ≤200/mm$^3$. In some embodiments, the HIV-infected individual has AIDS. In some embodiments, the HIV-infected individual has AIDS-related complex (ARC). In certain embodiments, ARC is defined as the presence of two successive CD4+ cell counts below 200/mm$^3$ and at least two of the following signs or symptoms: oral hairy leukoplakia, recurrent oral candidiasis, weight loss of at least 15 lb or 10% of body weight within last six months, multidermatomal herpes zoster, temperature above 38.5° C. for more than 14 consecutive days or more than 15 days in a 30-day period, or diarrhea with more than three liquid stools per day for at least 30 days [see, e.g., Yamada et al., *Clin. Diagn. Virol.* (1993) 1:245-256].

In some embodiments, the individual in need thereof is undergoing immunosuppressive therapy. In some embodiments, the immunosuppressive therapy comprises administering an immunosuppressive agent [see, e.g., Mueller, *Ann. Thorac. Surg.* (2004) 77:354-362; and Krieger and Emre, *Pediatr. Transplantation* (2004) 8:594-599]. In some embodiments, the immunosuppressive therapy comprises administering an immunosuppressive agent selected from the group consisting of: corticosteroids (for example, prednisone and the like), calcineurin inhibitors (for example, cyclosporine, tacrolimus, and the like), antiproliferative agents (for example, azathioprine, mycophenolate mofetil, sirolimus, everolimus, and the like), T-cell depleting agents (for example, OKT®3 monoclonal antibody (mAb), anti-CD3 immunotoxin FN18-CRM9, Campath-1H (anti-CD52) mAb, anti-CD4 mAb, anti-T cell receptor mAb, and the like), anti-IL-2 receptor (CD25) mAb (for example, basiliximab, daclizumab, and the like), inhibitors of co-stimulation (for example, CTLA4-Ig, anti-CD 154 (CD40 ligand) mAb, and the like), deoxyspergualin and analogs thereof (for example, 15-DSG, LF-08-0299, LF14-0195, and the like), leflunomide and analogs thereof (for example, leflunomide, FK778, FK779, and the like), FTY720, anti-alpha-4-integrin monoclonal antibody, and anti-CD45 RB monoclonal antibody. In some embodiments, the immunosuppressive agent and said salt or pharmaceutical composition are administered in separate dosage forms. In some embodiments, the immunosuppressive agent and said salt or pharmaceutical composition are administered in a single dosage form.

In some embodiments, the individual in need thereof is undergoing immunosuppressive therapy after organ transplantation. In some embodiments, the organ is liver, kidney, lung, heart, or the like [see, e.g., Singh et al., *Transplantation* (2000) 69:467-472].

In some embodiments, the individual in need thereof is undergoing treatment for a rheumatic disease. In some embodiments, the rheumatic disease is systemic lupus erythematosus or the like.

In some embodiments, the salt or the pharmaceutical composition inhibits JC virus infection of human glial cells 9. Hypertension Serotonin has been observed to play an important role in the regulation of vascular tone, vasoconstriction, and pulmonary hypertension (Deuchar, G. et al. *Pulm. Pharmacol. Ther.* 18(1):23-31. 2005; and Marcos, E. et al. *Circ. Res.* 94(9):1263-70 2004). Ketanserin, a 5-HT$_{2A}$ inverse agonist, have been demonstrated to protect against circulatory shocks, intracranial hypertension, and cerebral ischemia during heatstroke (Chang, C. et al. Shock 24(4): 336-340 2005); and to stabilize blood pressure in spontaneously hypertensive rats (Miao, C. *Clin. Exp. Pharmacol. Physiol.* 30(3): 189-193). Mainserin, a 5-HT$_{2A}$ inverse agonist, has been shown to prevent DOCA-salt induced hypertension in rats (Silva, A. *Eur, J. Pharmacol.* 518(2-3): 152-7 2005).

10. Pain

5-HT$_{2A}$ inverse agonists are also effective for the treatment of pain. Sarpogrelate has been observed to provide a significant analgesic effect both on thermal induced pain in rats after intraperitoneal administration and on inflammatory pain in rats after either intrathecal or intraperitoneal administration (Nishiyama, T. *Eur. J. Pharmacol.* 516:18-22 2005). This same 5-HT$_{2A}$ inverse agonist in humans has been shown to be an effective treatment for lower back pain, leg pain and numbness associated with sciatica brought on by lumbar disc herniation (Kanayama, M. et al. *J. Neurosurg.: Spine* 2:441-446 2005).

Pharmaceutical Compositions

A further aspect of the present invention pertains to pharmaceutical compositions comprising one or more salts as described herein and one or more pharmaceutically acceptable carriers. Some embodiments pertain to pharmaceutical compositions comprising a salt of the present invention and a pharmaceutically acceptable carrier.

Some embodiments of the present invention include a method of producing a pharmaceutical composition comprising admixing at least one salt according to any of the salt embodiments disclosed herein and a pharmaceutically acceptable carrier.

Formulations may be prepared by any suitable method, typically by uniformly mixing the active salt(s) with liquids or finely divided solid carriers, or both, in the required proportions and then, if necessary, forming the resulting mixture into a desired shape.

Conventional excipients, such as binding agents, fillers, acceptable wetting agents, tabletting lubricants and disintegrants may be used in tablets and capsules for oral administration. Liquid preparations for oral administration may be in the form of solutions, emulsions, aqueous or oily suspensions and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives and flavorings and colorants may be added to the liquid preparations. Parenteral dosage forms may be prepared by dissolving the salt of the invention in a suitable liquid vehicle and filter sterilizing the solution before filling and sealing an appropriate vial or ampule. These are just a few examples of the many appropriate methods well known in the art for preparing dosage forms.

A salt of the present invention can be formulated into pharmaceutical compositions using techniques well known to those in the art. Suitable pharmaceutically-acceptable carriers, outside those mentioned herein, are known in the art; for example, see Remington, *The Science and Practice of Pharmacy*, 20$^{th}$ Edition, 2000, Lippincott Williams & Wilkins, (Editors: Gennaro et al.)

While it is possible that, for use in the prophylaxis or treatment, a salt of the invention may, in an alternative use, be administered as a raw or pure chemical, it is preferable however to present the salt or active ingredient as a pharmaceutical formulation or composition further comprising a pharmaceutically acceptable carrier.

The invention thus further provides pharmaceutical formulations comprising a salt of the invention or a solvate, hydrate or derivative thereof together with one or more pharmaceutically acceptable carriers thereof and/or prophylactic ingredients. The carrier(s) must be "acceptable" in the sense of being compatible with the other ingredients of the formulation and not overly deleterious to the recipient thereof. Typical procedures for making and identifying suitable hydrates and solvates, outside those mentioned herein, are well known to those in the art; see for example, pages 202-209 of K. J. Guillory, "Generation of Polymorphs, Hydrates, Solvates, and Amorphous Solids," in: *Polymorphism in Pharmaceutical Solids*, ed. Harry G. Brittan, Vol. 95, Marcel Dekker, Inc., New York, 1999, incorporated herein by reference in its entirety.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation, insufflation or by a transdermal patch. Transdermal patches dispense a drug at a controlled rate by presenting the drug for absorption in an efficient manner with a minimum of degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The salts of the invention, together with a conventional adjuvant, carrier, or diluent, may thus be placed into the form of pharmaceutical formulations and unit dosages thereof and in such form may be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active salts or principles and such unit dosage forms may contain any suitable effective amount of the active ingredient commensurate with the intended daily dosage range to be employed.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, *acacia*, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable pharmaceutically acceptable carrier.

Salts of the present invention or a solvate, hydrate or physiologically functional derivative thereof can be used as active ingredients in pharmaceutical compositions, specifically as $5\text{-HT}_{2A}$ receptor modulators. By the term "active ingredient" is defined in the context of a "pharmaceutical composition" and is intended to mean a component of a pharmaceutical composition that provides the primary pharmacological effect, as opposed to an "inactive ingredient" which would generally be recognized as providing no pharmaceutical benefit.

The dose when using the salts of the present invention can vary within wide limits and as is customary and is known to the physician, it is to be tailored to the individual conditions in each individual case. It depends, for example, on the nature and severity of the illness to be treated, on the condition of the patient, on the salt employed or on whether an acute or chronic disease state is treated or prophylaxis is conducted or on whether further active salts are administered in addition to the salts of the present invention. Representative doses of the present invention include, but not limited to, about 0.001 mg to about 5000 mg, about 0.001 mg to about 2500 mg, about 0.001 mg to about 1000 mg, 0.001 mg to about 500 mg, 0.001 mg to about 250 mg, about 0.001 mg to 100 mg, about 0.001 mg to about 50 mg and about 0.001 mg to about 25 mg. Multiple doses may be administered during the day, especially when relatively large amounts are deemed to be needed, for example 2, 3 or 4 doses. Depending on the individual and as deemed appropriate from the patient's physician or caregiver it may be necessary to deviate upward or downward from the doses described herein.

The amount of active ingredient, or an active salt or derivative thereof, required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. In some circumstances, these extrapolations may merely be based on the weight of the animal model in comparison to another, such as a mammal, preferably a human, however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular salt employed, whether a drug delivery system is utilized, on whether an acute or chronic disease state is being treated or prophylaxis is conducted or on whether further active salts are administered in addition to the salts of the present invention and as part of a drug combination. The dosage regimen for treating a disease condition with the salts and/or compositions of this invention is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods of this invention.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. The daily dose can be divided, especially when relatively large amounts are administered as deemed appropriate, into several, for example 2, 3 or 4 part administrations. If appropriate, depending on individual behavior, it may be necessary to deviate upward or downward from the daily dose indicated.

The salts of the present invention can be administered in a wide variety of oral and parenteral dosage forms. It will be obvious to those skilled in the art that the following dosage forms may comprise, as the active component, either a salt of the invention or a solvate or hydrate thereof.

For preparing pharmaceutical compositions from the salts of the present invention, the selection of a suitable pharmaceutically acceptable carrier can be either solid, liquid or a mixture of both. Solid form preparations include powders, tablets, pills, capsules, cachets, suppositories and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted to the desire shape and size. The powders and tablets may contain varying percentage amounts of the active salt. A representative amount in a powder or tablet may contain from 0.5 to about 90 percent of the active salt; however, an artisan would know when amounts outside of this range are necessary. Suitable carriers for powders and tablets are magnesium carbonate, magnesium stearate, talc, sugar, lactose, pectin, dextrin, starch, gelatin, tragacanth, methylcellulose, sodium carboxymethylcellulose, a low melting wax, cocoa butter and the like. The term "preparation" is intended to include the formulation of the active salt with encapsulating material as carrier providing a capsule in which the active component, with or without carriers, is surrounded by a carrier, which is thus in association with it. Similarly, cachets and lozenges are included. Tablets, powders, capsules, pills, cachets and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The salts according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The pharmaceutical compositions may take such forms as suspensions, solutions, or emulsions in oily or aqueous vehicles and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous formulations suitable for oral use can be prepared by dissolving or suspending the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well-known suspending agents.

Also included are solid form preparations which are intended to be converted, shortly before use, to liquid form preparations for oral administration. Such liquid forms include solutions, suspensions and emulsions. These preparations may contain, in addition to the active component, colorants, flavors, stabilizers, buffers, artificial and natural sweeteners, dispersants, thickeners, solubilizing agents and the like.

For topical administration to the epidermis the salts according to the invention may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active agent in a flavored base, usually sucrose and *acacia* or tragacanth; pastilles comprising the active ingredient in an inert base such as gelatin and glycerin or sucrose and *acacia*; and mouthwashes comprising the active ingredient in a suitable liquid carrier.

Solutions or suspensions are applied directly to the nasal cavity by conventional means, for example with a dropper, pipette or spray. The formulations may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant. If the salts of the present invention or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the salts of the present invention as an aerosol can be prepared by processes well known to the person skilled in the art. For their preparation, for example, solutions or dispersions of the salts of the present invention in water, water/alcohol mixtures or suitable saline solutions can be employed using customary additives, for example benzyl alcohol or other suitable preservatives, absorption enhancers for increasing the bioavailability, solubilizers, dispersants and others and, if appropriate, customary propellants, for example include carbon dioxide, CFCs, such as, dichlorodifluoromethane, trichlorofluoromethane, or dichlorotetrafluoroethane; and the like. The aerosol may conveniently also contain a surfactant such as lecithin. The dose of drug may be controlled by provision of a metered valve.

In formulations intended for administration to the respiratory tract, including intranasal formulations, the salt will generally have a small particle size for example of the order of 10 microns or less. Such a particle size may be obtained by means known in the art, for example by micronization. When desired, formulations adapted to give sustained release of the active ingredient may be employed.

Alternatively the active ingredients may be provided in the form of a dry powder, for example, a powder mix of the salt in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

Pharmaceutically acceptable salts including pharmaceutically acceptable acid addition salts may be prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfiric, tartaric, oxalic, p-toluenesulfonic and the like, such as those pharmaceutically acceptable salts listed in *Journal of Pharmaceutical Sciences*, 66:1-19 (1977), incorporated herein by reference in its entirety.

The acid addition salts may be obtained as the direct products of compound synthesis. In the alternative, the free base may be dissolved in a suitable solvent containing the appropriate acid and the salt isolated by evaporating the solvent or otherwise separating the salt and solvent. The salts of this invention may form solvates with standard low molecular weight solvents using methods known to the skilled artisan.

Salts of the present invention can be converted to "pro-drugs." The term "pro-drugs" refers to salts that have been modified with specific chemical groups known in the art and when administered into an individual these groups undergo biotransformation to give the parent compound. Pro-drugs can thus be viewed as salts of the invention containing one or more specialized non-toxic protective groups used in a transient manner to alter or to eliminate a property of the salt. In one general aspect, the "pro-drug" approach is utilized to facilitate oral absorption. A thorough discussion is provided in T. Higuchi and V. Stella, Pro-drugs as Novel Delivery Systems Vol. 14 of the A.C.S. Symposium Series; and in *Bioreversible Carriers in Drug Design*, ed. Edward B. Roche, American Pharmaceutical Association and Pergamon Press, 1987, both of which are hereby incorporated by reference in their entirety.

Some embodiments of the present invention include a method of producing a pharmaceutical composition for "combination-therapy" comprising admixing at least one salt according to any of the salt embodiments disclosed herein, together with at least one known pharmaceutical agent as described herein and a pharmaceutically acceptable carrier.

It is noted that when the 5-$HT_{2A}$ receptor modulators are utilized as active ingredients in a pharmaceutical composition, these are not intended for use only in humans, but in other non-human mammals as well. Indeed, recent advances in the area of animal health-care mandate that consideration be given for the use of active agents, such as 5-$HT_{2A}$ receptor modulators, for the treatment of an 5-$HT_{2A}$-associated disease or disorder in companionship animals (e.g., cats, dogs, etc.) and in livestock animals (e.g., cows, chickens, fish, etc.) Those of ordinary skill in the art are readily credited with understanding the utility of such salts in such settings.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Illustrated syntheses of the present invention are shown Scheme 1 where the symbols have the same definitions as used throughout this disclosure.

The syntheses are further illustrated by the following examples. The following examples are provided to further define the invention without, however, limiting the invention to the particulars of these examples. The compounds and salts thereof described herein, supra and infra, are named according to the CS ChemDraw Ultra Version 7.0.1, AutoNom version 2.2, or CS ChemDraw Ultra Version 9.0.7. In certain instances common names are used and it is understood that these common names would be recognized by those skilled in the art.

Chemical shifts of proton nuclear magnetic resonance ($^1$H NMR) spectra are given in parts per million (ppm) with the residual solvent signal used as reference. NMR abbreviations are used as follows: s=singlet, d=doublet, t=triplet, q=quartet, m=multiplet, bs=broad singlet.

LCMS spec: HPLC-pumps: LC-10AD VP, Shimadzu Inc.; HPLC system controller: SCL-10A VP, Shimadzu Inc; UV-Detector: SPD-10A VP, Shimadzu Inc; Autosampler:

CTC HTS, PAL, Leap Scientific; Mass spectrometer: API 150EX with Turbo Ion Spray source, AB/MDS Sciex; Software: Analyst 1.2.

Example 1

Preparation of 4-Chloro-1-methyl-1H-pyrazole-3-carboxylic Acid

Step A: Preparation of Ethyl 4-Ethoxy-2-oxo-3-butenoate

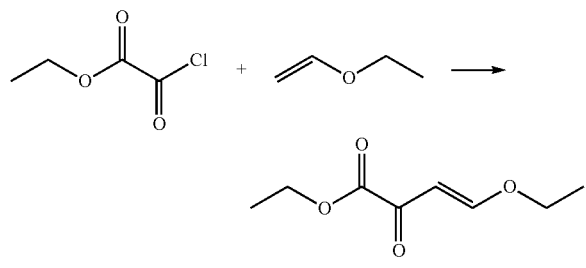

To a solution of triethylamine (444 mL, 4.39 mol) in ethyl vinyl ether (1.7 L) under a nitrogen atmosphere was added ethyl oxalyl chloride (500 g, 3.66 mol) dropwise over 1 h. After complete addition, the reaction became exothermic and started to reflux. Once the exotherm had subsided the reaction mixture was allowed to stir at room temperature for an additional 2 h. After complete reaction, the mixture was diluted with MTBE (1.2 L) and the resultant triethylammonium chloride precipitate was filtered and washed twice with MTBE (2×500 mL). The combined filtrates were concentrated under reduced pressure to give crude ethyl-4-ethoxy-2-oxo-3-butenoate (655 g) as viscous orange oil. This oil was used crude in the subsequent reaction. $^1$H-NMR (400 MHz, DMSO-d$_6$) δ 7.85 (d, J=12.6 Hz, 1H), 5.99 (d, J=12.6 Hz, 1H), 4.24 (q, J=7.0 Hz, 2H), 4.11 (q, J=7.0 Hz, 2H), 1.30-1.20 (m, 6H).

Step B: Preparation of 1H-Pyrazole-3-carboxylic Acid Ethyl Ester

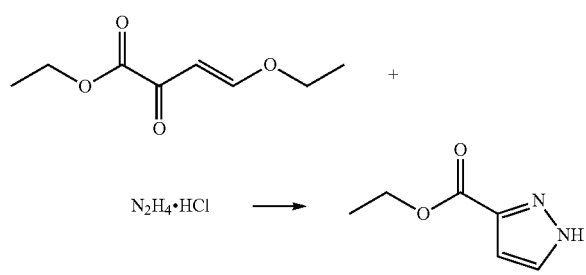

A suspension of hydrazine hydrochloride (250 g, 3.65 mol) in methanol (1.5 L) was heated to reflux under nitrogen. At reflux, crude ethyl 4-ethoxy-2-oxo-3-butenoate (655 g, 3.65 mol) was added dropwise over 2 h. After complete addition, the reaction was allowed to cool to room temperature with stirring. After 2 h, the reaction was complete and it was cooled to 5° C. (ice bath) and the resulting precipitate was filtered and then washed with methanol (100 mL) to provide the first crop of the title compound (containing unreacted hydrazine hydrochloride, which was later removed by washing with water). The combined filtrates were concentrated under reduced pressure to give a brown syrupy residue (about 400 mL). Water (1.2 L) was added to the syrup and the mixture stirred for 30 min. The resulting solid was filtered under suction to provide a second crop of the title compound. The two product crops were combined and washed with water (2×100 mL) to afford the title compound as a beige solid (241 g, 47% over two steps) containing up to 15% w/w of 1H-pyrazole-3-carboxylic acid methyl ester. $^1$H-NMR (400 MHz, DMSO-d$_6$) δ 13.57 (bs, 1H), 7.82 (m, 1H), 6.76 (m, 1H), 4.26 (q, J=7.1 Hz, 2H), 3.80 (s, methyl ester impurity), 1.29 (t, J=7.1 Hz, 3H).

Step C: Preparation of 4-Chloro-1H-Pyrazole-3-carboxylic Acid Ethyl Ester

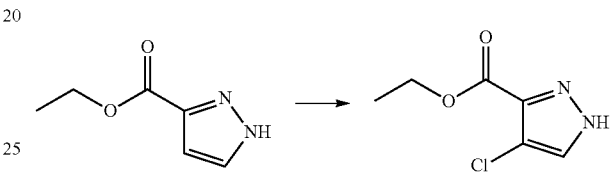

A 5 L flange flask fitted with an overhead stirrer, condenser and temperature probe was charged with 1H-pyrazole-3-carboxylic acid ethyl ester (326 g, 2.33 mol) and N,N-dimethylformamide (1.86 L). The suspension was stirred and heated to 40° C. internal temperature under nitrogen causing the precipitate to dissolve. Once dissolved, solid N-chlorosuccinimide (NCS) (342 g, 2.56 mol) was added portionwise (10-15 g portions) over 2 h, maintaining the reaction temperature <45° C. When all the NCS had been added, the reaction was allowed to cool slowly to 20° C. over 16 h. Once complete consumption of starting material had been achieved, the reaction mixture was cooled to about 15° C. and then with vigorous stirring, water (1.9 L) was added over 10 minutes. The suspension was stirred for a further 20 min and then filtered through a sinter funnel under suction. The filter cake was carefully washed twice with water (2×750 mL) and then with heptanes (1×500 mL). The filter cake was air dried and then transferred to a vacuum oven and dried overnight (60° C., 9 mBar). The title compound was isolated as an off-white solid (330 g, 1.89 mol, 81%) containing an impurity, 4-chloro-1H-pyrazole-3-carboxylic acid methyl ester. $^1$H-NMR (400 MHz, DMSO-d$_6$): δ 14.3 (bs, 1H, minor tautomer), 13.8 (bs, 1H, major tautomer), 7.95 (bs, 1H, major tautomer), 7.77 (bs, 1H, minor tautomer), 4.40-4.20 (m, 2H, overlapping tautomers), 3.40-3.25 (bs, methyl ester impurity), 1.40-1.20 (m, 3H, overlapping tautomers).

Step D: Preparation of 4-Chloro-1-methyl-1H-pyrazole-3-carboxylic Acid Ethyl Ester

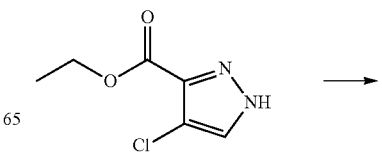

-continued

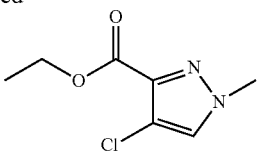

A 5 L flange flask fitted with an overhead stirrer, pressure equalizing dropping funnel, condenser and temperature probe was charged with 4-chloro-1H-pyrazole-3-carboxylic acid ethyl ester (330 g, 1.89 mol), anhydrous potassium carbonate (784 g, 5.67 mol) and 2-methyl tetrahydrofuran (2 L). The dropping funnel was charged with iodomethane (537 g, 3.78 mol), as a thin stream to the reaction mixture over 1 h. Following complete addition, the reaction was stirred at 20° C. for 16 h. Once the reaction was complete, the suspension was filtered through a sinter funnel and the cake washed twice with tetrahydrofuran (2×660 mL). The combined filtrates were concentrated to about 10% of the original volume under reduced pressure then heptane (660 mL) was added with mixing. After aging for 10 minutes, the light brown precipitate was filtered under suction, and the cake was washed with further heptanes (660 mL) and air-dried. The cake was further dried under reduced pressure (60° C., 9 mBar) to afford the title compound as a light-brown crystalline solid (331 g, 1.696 mol, 93%) containing an impurity, 4-chloro-1-methyl-1H-pyrazole-3-carboxylic acid methyl ester. $^1$H-NMR (400 MHz, DMSO-d$_6$): δ 8.12 (s, 1H), 4.27 (q, J=7.1 Hz, 2H), 3.89 (s, 3H), 3.34 (s, methyl ester impurity), 1.28 (t, J=7.1 Hz, 3H).

Step E: Preparation of 4-Chloro-1-methyl-1H-pyrazole-3-carboxylic Acid

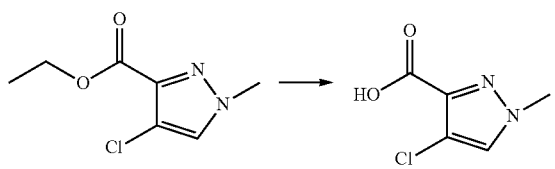

Method 1: A 5 L flange flask fitted with an overhead stirrer, pressure equalizing dropping funnel and a temperature probe was charged with 4-chloro-1-methyl-1H-pyrazole-3-carboxylic acid ethyl ester (309 g, 1.640 mol) and propan-2-ol (1.55 L). The mixture was gently warmed to an internal temperature of 45° C. and then a solution of NaOH (131 g, 3.28 mol) in deionized water (930 mL) was added over 30 min. The mixture was stirred and heated at 45° C. for an additional 2.5 h until all the starting material had been consumed. The reaction mixture was partially concentrated under reduced pressure, and the propan-2-ol removed. The remaining solution was added with stirring to a solution of concentrated HCl (520 mL) in deionized water (1.5 L). The resulting white precipitate was stirred at room temperature for 48 h. The precipitate was then filtered under suction and the crude product combined with two other batches prepared as above. The wet, crude product (800 g) was recrystallized by dissolving in glacial acetic acid (2.8 L) with heating to 80° C. Once dissolved, deionized water (1 L) was added and then the hot solution was poured, with vigorous stirring into water (3 L). Once cooled-to-room temperature, the grey precipitate was filtered under suction, washed with additional water (2×1 L) and heptanes (1×500 mL) and then transferred to a vacuum oven for further drying (24-36 h, 70° C., 9 mBar) to give the title compound (363 g, 54%). The filtrate solution (AcOH/H$_2$O) was concentrated under reduced pressure, until more precipitate appeared which was filtered under suction on a sinter funnel. The filter cake was washed with water (1 L) and the off-white solid dried in a vacuum oven (24 h, 70° C., 9 mBar) to leave a second crop of the title compound (103 g, 15%). The combined filtrates were evaporated to dryness and the residue recrystallized from hot deionized water (2.5 L, 85° C.). Upon cooling to 10° C., the white precipitate was filtered under suction and then dried in a vacuum oven (24 h, 70° C., 9 mBar) to leave a third crop of the title compound (39 g, 6%). A final evaporation of aq. HCl solution and any other remaining filtrates provided additional product (13%). Therefore a total of 592 g of the title compound (88%) was isolated. $^1$H-NMR (400 MHz, DMSO-d$_6$): δ 12.95 (s, 1H), 8.08 (s, 1H), 3.90 (s, 3H).

Method 2: A 10 L flange flask fitted with an overhead stirrer, pressure equalizing dropping funnel and a temperature probe was charged with 4-chloro-1-methyl-1H-pyrazole-3-carboxylic acid ethyl ester (489 g, 2.593 mol) and 2-methyltetrahydrofuran (3 L). The mixture was warmed to 40° C., stirred until dissolved and then an aqueous solution of KOH (291 g, 5.185 mol) in deionized water (1.5 L) was added over 15 minutes. At this point, to assist stirring, additional water (1 L) was added and stirring was continued for 16 h. Once complete, the organic phase was separated and discarded. The basic aqueous phase was acidified by addition to cooled, vigorously stirred 4 M HCl (1.4 L). After complete addition, the precipitate was stirred for an additional 1 h at room temperature, filtered, washed with water (3×1 L), heptane (1 L) and then air-dried (2 h). The cake was further dried under reduced pressure (48 h, 80° C., 9 mBar) to afford the title compound as a white crystalline solid (384 g, 93%). $^1$H-NMR (400 MHz, DMSO-d$_6$): δ12.95 (s, 1H), 8.08 (s, 1H), 3.90 (s, 3H).

Example 2

Preparation of (S)-1-(4-Fluorophenyl)-2-(3-methylpiperazin-1-yl) ethanone hydrobromide

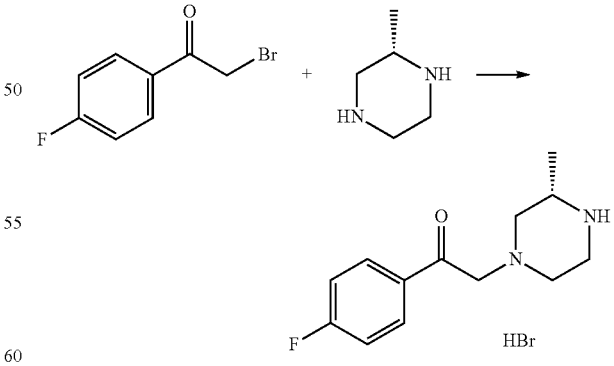

In a 5 L three-neck reactor equipped with a stirrer, a thermocouple, a cooling bath, an addition funnel and a nitrogen inlet was placed (S)-2-methylpiperazine (175 g, 1.753 mol) and isopropanol (3.2 L). The mixture was cooled and stirred well at 4° C. in an isopropanol/ice bath. 4'-Fluoro-2-bromoacetophenone (350 g, 1.613 mol) was added portion-wise (25 g each) at such a rate that the reaction temperature was kept at below 10° C. After the addition was completed, the reaction was allowed to warm to room temperature and stirred overnight. Isopropanol (500 mL) was then added over a period of 25 to 30 min. 1 h after the addition was completed, the reaction was warmed slowly to 45° C. The slurry was filtered. The solid was washed with isopropanol and dried in a vacuum oven at 40° C. to provide the title compound (417 g). LCMS m/z=373.1 [M+H]$^+$; $^1$H NMR (400 MHz, DMSO-d$_6$) δ 8.86 (bs, 2H), 8.06-8.14 (m, 2H), 7.34-7.42 (m, 2H), 4.08 (s, 2H), 3.25-3.40 (m, 2H), 2.97-3.05 (m, 3H), 2.62-2.68 (m, 1H), 2.41-2.46 (m, 1H), 1.28 (d, J=9, 3H).

Example 3

Preparation of (4-Chloro-1-methyl-1H-pyrazol-3-yl)(1H-imidazol-1-yl)methanone

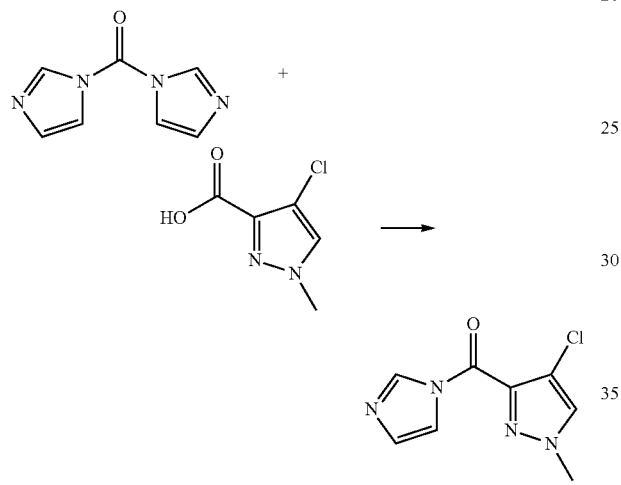

In a 5 L three-neck reactor equipped with a mechanical stirrer, a thermocouple, a heating mantle, a condenser, an addition funnel and a nitrogen inlet was placed 4-chloro-1-methyl-1H-pyrazole-3-carboxylic acid (201 g, 1.252 mol) and acetonitrile (2.0 L). Carbonyldiimidazole (198 g, 1.221 mol) was added slowly. After completion of the addition, acetonitrile (100 mL) was added to wash down the residual solids. The reaction mixture was heated to 55-57° C. for 1 h and cooled to 30-35° C. The product was used in Example 4 infra without further purification.

Example 4

Preparation of (S)-2-(4-(4-Chloro-1-methyl-1H-pyrazole-3-carbonyl)-3-methylpiperazin-1-yl)-1-(4-fluorophenyl)ethanone

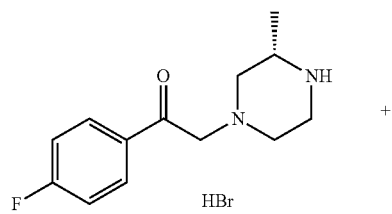

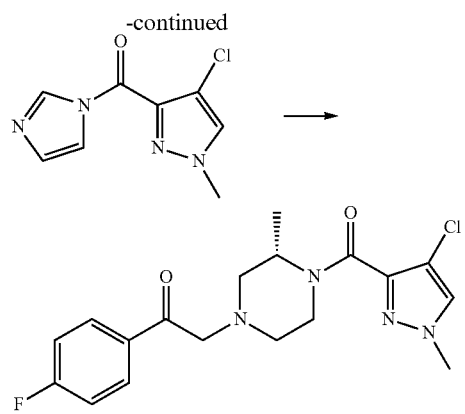

(S)-1-(4-Fluorophenyl)-2-(3-methylpiperazin-1-yl) ethanone hydrobromide (397 g, 1.252 mol) and 2-hydroxy pyridine (4.0 g) were added slowly to the reaction mixture described in Example 3, followed by triethylamine (190 g 1.878 mol). The solution became homogenous. After completion of addition, the reaction mixture was heated under nitrogen atmosphere at 65° C. overnight. The mixture was concentrated. The residue was diluted with water (1 L). The thick slurry was extracted with isopropyl acetate (2×500 mL). The isopropyl acetate layer was washed with NaOH solution (10%, 300 mL), water (250 mL), dried over magnesium sulfate (85 g), and concentrated under reduced pressure to provide the title compound (456 g, 96%). LCMS m/z=379.4 [M+H]$^+$.

Example 5

Preparation of (S)-2-(4-(4-Chloro-1-methyl-1H-pyrazole-3-carbonyl)-3-methylpiperazin-1-yl)-1-(4-fluorophenyl)ethanone hydrochloride

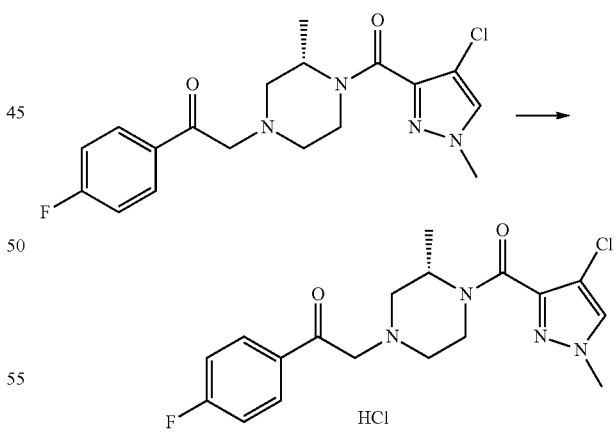

(S)-2-(4-(4-Chloro-1-methyl-1H-pyrazole-3-carbonyl)-3-methylpiperazin-1-yl)-1-(4-fluorophenyl) ethanone as crude freebase (456 g) was dissolved in ethanol (1.1 L) with gentle warming. Hydrochloric acid (1.25 M in EtOH, 1170 mL) was added. The reaction mixture was stirred at room temperature overnight. A thick precipitate of the hydrochloride salt separated out. The thick slurry was allowed to stand at room temperature overnight and heated slowly to 45° C. until the slurry became loose and easy to stir. The slurry was filtered warm (40° C.), washed with isopropanol (500 mL), and dried to give the title compound (201 g). A portion of the solvent (about 1100 mL) was removed from the mother liquors when more of the hydrochloride salt precipitated out. The slurry was cooled to room temperature and filtered. The solid was washed with isopropanol (2×300 mL) and dried to give an additional amount of the title compound (151 g), a total of 352 g (70%) combined. The enantiomeric excess as determined by chiral HPLC was 98%. LCMS m/z=379.3 [M+H]$^+$; $^1$H NMR (400 MHz, DMSO-d$_6$) δ 10.93-10.97 (bs, 1H), 8.08-8.12 (m, 2H), 7.47-7.51 (m, 2H), 4.87-5.21 (m, 3H), 4.58 (bs, 1.2H), 4.15 (bs, 0.8), 3.90 (s, 3H), 3.41-3.80 (m, 3H), 3.05-3.26 (bs, 2H), 1.50-1.52 (d, J=6 Hz, 3H).

Chiral HPLC Conditions

Column: ChiralPak ADH, 4.6×250 mm, 5 μm particle size, with pre-column filter

Mobile Phase: 0.05% diethylamine in hexane:methanol: ethanol (90:5:5)

Flow Rate: 1.0 mL/min

Sample Concentration: 0.2 mg/mL in mobile phase

Injection Volume: 20 μl

Column Temperature: 25° C.

Detector Wavelength 220 nm

Retention Times: S-enantiomer=32.6 min.; R-enantiomer=47.0 min.

Those skilled in the art will recognize that various modifications, additions, substitutions, and variations to the illustrative examples set forth herein can be made without departing from the spirit of the invention and are, therefore, considered within the scope of the invention. All documents referenced above, including, but not limited to, printed publications, and provisional and regular patent applications, are incorporated herein by reference in their entirety.

What is claimed is:

1. A hydrochloride salt of a compound of Formula (I):

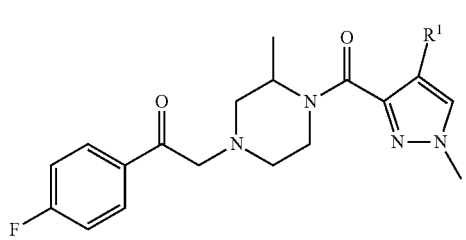

(I)

wherein:

R$^1$ is halogen.

2. The hydrochloride salt according to claim 1, wherein said compound of Formula (I) is the S enantiomer.

3. The hydrochloride salt according to claim 1, wherein R$^1$ is chloro.

4. The hydrochloride salt according to claim 1, wherein said hydrochloride salt is (S)-2-(4-(4-chloro-1-methyl-1H-pyrazole-3-carbonyl)-3-methylpiperazin-1-yl)-1-(4-fluorophenyl)ethanone hydrochloride, represented by the following structure:

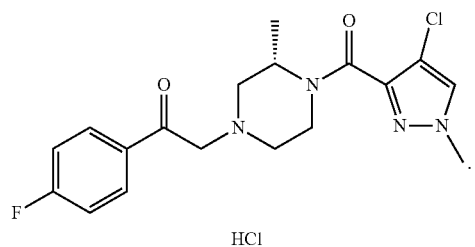 [SMILES: C[C@H]1CN(CC(=O)c2ccc(F)cc2)CCN1C(=O)c1nn(C)cc1Cl ; Cl]

HCl

5. A pharmaceutical composition comprising the hydrochloride salt according to any one of claims 1 to 4 together with a pharmaceutically acceptable carrier.

6. A process for preparing a composition comprising admixing the hydrochloride salt according to any one of claims 1 to 4 and a pharmaceutically acceptable carrier.

7. A process for preparing a compound of Formula (I):

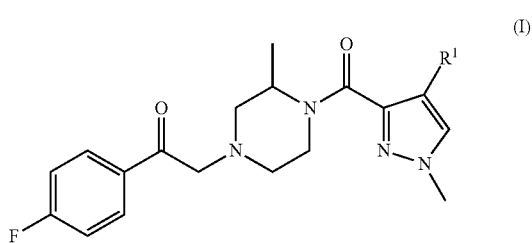

(I)

or a salt thereof, comprising:

(a) reacting a compound of Formula (VI):

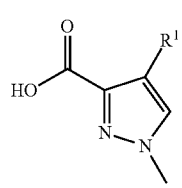

(VI)

or a salt thereof, with a compound of Formula (VII):

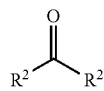

(VII)

or a salt thereof, to form a compound of Formula (III):

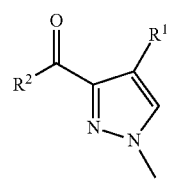

(III)

or a salt thereof;

(b) reacting a compound of Formula (IV):

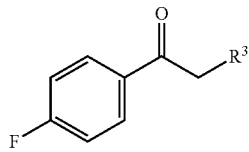

with a compound of Formula (V):

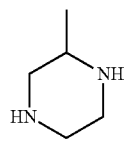

or a salt thereof, to form a compound of Formula (II):

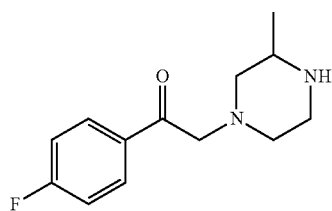

or a salt thereof; and (c) reacting said compound of Formula (II) or a salt thereof, with said compound of Formula (III) or a salt thereof, to form said compound of Formula (I) or a salt thereof;

wherein:

$R^1$ is a halogen $R^2$ is a leaving group; and $R^3$ is a halogen;

provided that $R^2$ is a leaving group other than 3H-[1,2,3]triazolo[4,5-b]pyridin-3-yloxy.

8. A process for preparing a compound of Formula (I):

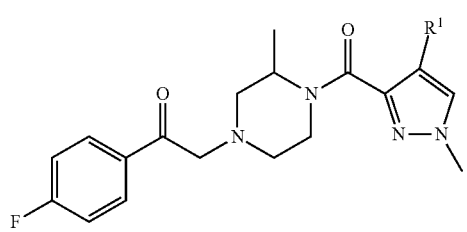

or a salt thereof, wherein:

$R^1$ is halogen;

comprising reacting a compound of Formula (II):

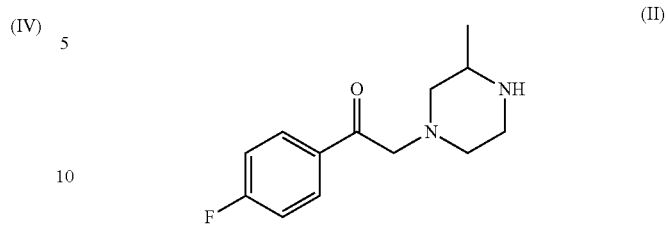

or a salt thereof, with a compound of Formula (III):

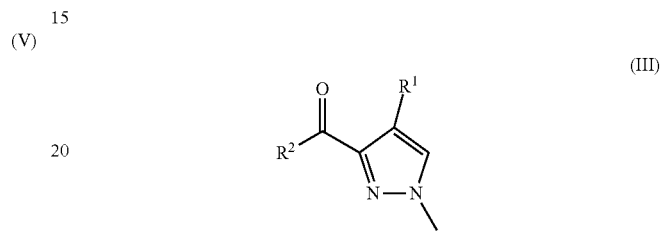

or a salt thereof, wherein:

$R^2$ is a leaving group;

to form said compound of Formula (I) or a salt thereof; provided that $R^2$ is a leaving group other than 3H-[1,2,3]triazolo[4,5-b]pyridin-3-yloxy.

9. The process according to claim 8, wherein said compound of Formula (I) is the S enantiomer.

10. The process according to claim 8 or 9, wherein $R^1$ is chloro and $R^2$ is 1H-imidazol-1-yl.

11. The process according to claim 8 or 9, wherein said reacting a compound of Formula (II) or a salt thereof, with a compound of Formula (III) or a salt thereof is carried out in the presence of a base.

12. The process according to claim 8 or 9, wherein said reacting a compound of Formula (II) or a salt thereof, with a compound of Formula (III) or a salt thereof is carried out in the presence of a catalyst.

13. The process according to claim 8 or 9, wherein said reacting a compound of Formula (II) or a salt thereof, with a compound of Formula (III) or a salt thereof is carried out at a temperature of about 20° C. to about reflux temperature.

14. The process according to claim 8 or 9, wherein said reacting a compound of Formula (II) or a salt thereof, with a compound of Formula (III) or a salt thereof is carried out in an amide-forming solvent.

15. A process for preparing a salt of a compound of Formula (I):

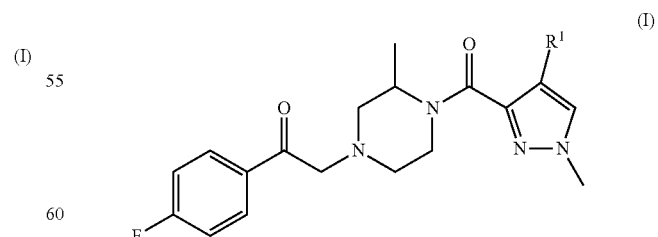

wherein:

$R^1$ is halogen;

comprising reacting said compound of Formula (I) with a salt-forming acid to form said salt of a compound of Formula (I).

16. The process according to claim 15, wherein said compound of Formula (I) is the S enantiomer.

17. The process according to claim 15 or 16, wherein said salt of a compound of Formula (I) is the hydrochloride salt.

18. The process according to claim 15 or 16, wherein $R^1$ is chloro.

19. The process according to claim 15 or 16, wherein said reacting said compound of Formula (I) with a salt-forming acid is carried out in a salt-forming solvent.

20. The process according to claim 15 or 16, wherein said reacting said compound of Formula (I) with a salt-forming acid is carried out at a temperature of about −10° C. to about reflux temperature.

21. The process according to claim 15 or 16, wherein said salt-forming acid is hydrochloric acid.

* * * * *